United States Patent [19]

Bach et al.

[11] 4,301,065

[45] Nov. 17, 1981

[54] NOVEL POLYPEPTIDES HAVING THYMIC ACTIVITY OR AN ANTAGONISTIC ACTIVITY AND PROCESSES FOR THEIR SYNTHESIS

[75] Inventors: Jean-Francois Bach, Paris; Mireille Dardenne; Jean-Marie Pleau, both of Palaiseau; Jean Hamburger, Paris; Evanghelos Bricas, Antony; Jean Martinez, Montpellier; Didier Blanot, Bures S. Yvette; Geneviève Auger, Limours, all of France

[73] Assignee: Agence Nationale de Valorisation de la Recherche (ANVAR), Paris, France

[21] Appl. No.: 909,163

[22] Filed: May 24, 1978

[30] Foreign Application Priority Data

May 25, 1977 [FR] France .................................. 77 15963
Apr. 21, 1978 [FR] France .................................. 78 11870

[51] Int. Cl.³ .......................................... C07C 103/52
[52] U.S. Cl. ............................................. 260/112.5 R
[58] Field of Search .................................. 260/112.5 R

[56] References Cited

U.S. PATENT DOCUMENTS 4,002,602  1/1977  Goldstein ..................... 260/112.5 R
4,002,740  1/1977  Goldstein et al. ............ 260/112.5 R
4,077,949  3/1978  Goldstein ..................... 260/112.5 R
4,115,375  9/1978  Pedersen ...................... 260/112.5 R
4,148,886  4/1979  Bach et al. ................... 260/112.5 R

OTHER PUBLICATIONS

Academie des Sciences, 283, 1976, pp. 1605–1609.
C. R. Acad. Sc. Paris, 283, 29 Nov. 1976, 1605–1607.
Nature, 266, 1977, 55–57.

Primary Examiner—Delbert K. Phillips
Attorney, Agent, or Firm—Weiser, Stapler & Spivak

[57] ABSTRACT

The invention is concerned with novel polypeptides and processes for the synthesis thereof.

It is concerned with compounds having the sequence

X-Gln-Gly-Gly-Y in which Y represents -Ser-Asn and X represents Ser-, Lys-Ser-, Ala-Lys-Ser-, Glx-Ala-Lys-Ser-; Glx representing Pyro-Glu or Gln; and when X represents Glx-Ala-Lys-Ser-, Y may in addition represent -Ser; as well as their derivatives comprising one or two modified amino acids, with the exception of the unmodified compound PyroGlu-Ala-Lys-Ser-Gln-Gly-Ser-Asn.

These polypeptides are useful as medicines.

4 Claims, 3 Drawing Figures

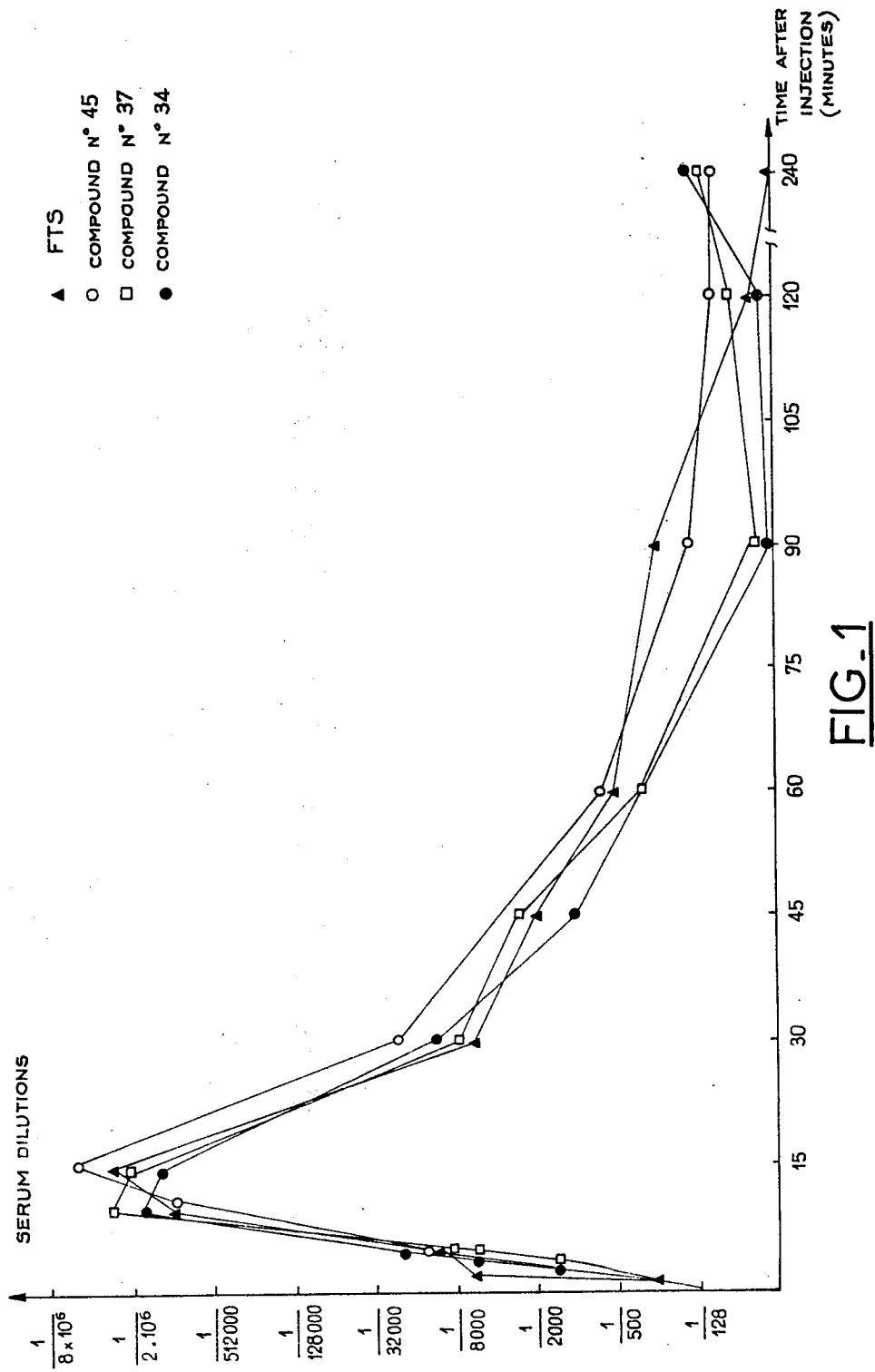

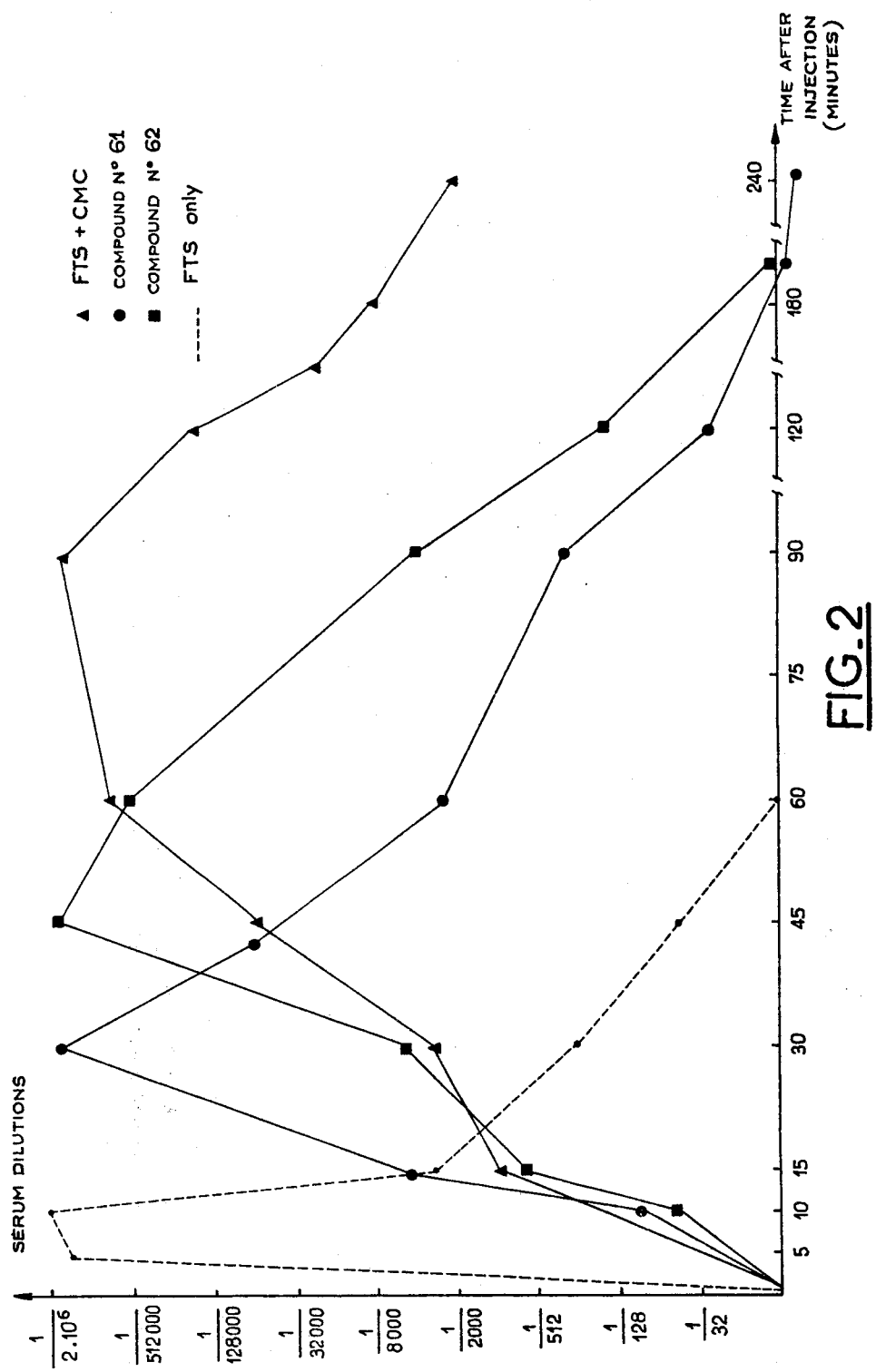

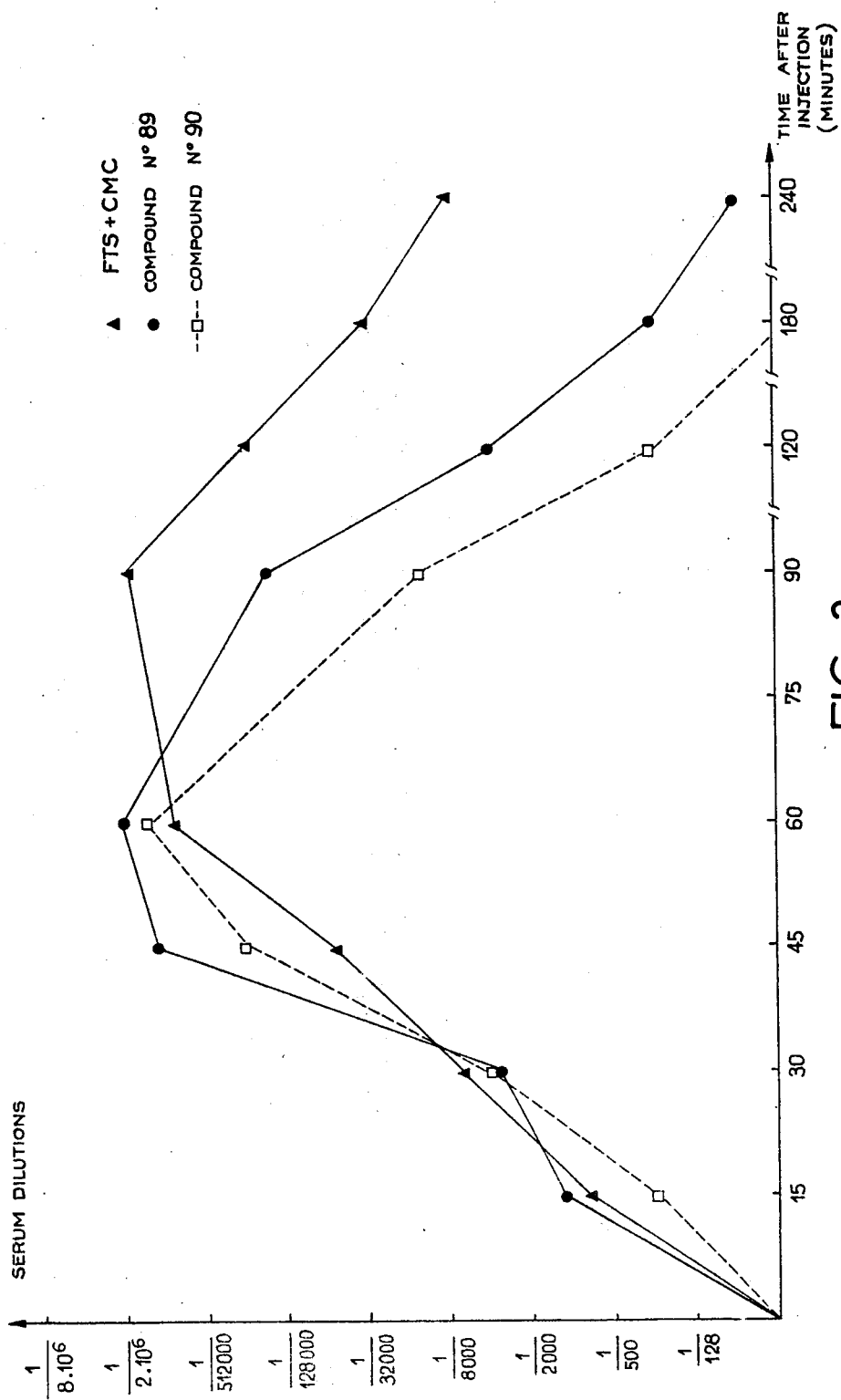
FIG_3

NOVEL POLYPEPTIDES HAVING THYMIC ACTIVITY OR AN ANTAGONISTIC ACTIVITY AND PROCESSES FOR THEIR SYNTHESIS

The present invention relates to novel peptide compounds, of which the chemical structure is related to that of the polypeptide hormone having a thymic activity, isolated from the blood serum of pig, processes for the preparation of the novel compounds by a chemical synthesis procedure and the application of these novel compounds for therapeutic purposes.

It has been well established that the T Lymphocytes acquire their immunocompetence under the influence of the thymus. This differentiating action of the thymus has formed the subject of numerous research procedures since the discovery of the immuno-suppressive effects of neonatal thymectomy. Experiments which show the respiration of the immunitary competence of mice thymectomised at birth by thymus grafts placed in diffusion chambers impermeable to the cells or by acellular thymic extracts have suggested that the thymus plays the part of an endocrine gland and prepares a hormone which is introduced into the blood circulation.

The isolation and the characterisation of a hormone, which is referred to as "seric thymic factor" (STF), present in the serum of several species of mammals, particularly pigs, have formed the subject of recent publications.

It has thus been shown that the seric thymic factor is a nonapeptide, which is characterised by the sequence of the following amino acids:

PyroGlu-Ala-Lys-Ser-Gln-Gly-Gly-Ser-Asn (I)

Now the chemical synthesis of the seric thymic factor having the structure (I) as indicated above has just been carried out, as well as that of a family of peptide compounds of related structure, including therein that of another active form of the seric thymic factor, corresponding to the following structure Gln-Ala-Lys-Ser-Gln-Gly-Gly-Ser-Asn (II)

These synthesis operations have made it possible either to obtain polypeptides having a thymic activity equal to or better than that of the natural hormone, but having a more prolonged effect due to their resistance to the action of enzymes, which degrade the thymic hormone in the organism, or to effect the partial transformation of the chemical structure of the natural hormone, leading to compounds which eventually show an antagonistic or inhibiting action with respect to the thymic hormone.

Accepting that the action of the thymic hormone permits the development of immunizing defense reactions which lead to the rejection of the grafts, an antagonistic or inhibiting action which is exerted by such compounds may eventually play an important part in the prevention of a rejection of the grafts.

The invention is concerned with the polypeptide compounds conforming to the sequence:

Glx-Ala-Lys-Ser-Gln-Gly-Gly-Ser-Asn in which Glx represents PyroGlu or Gln, their derivatives comprising 1 or 2 modified amino acids, and the hexapeptides, heptapeptides and octapeptides of these compounds, which preserve their C-terminal or N-terminal sequence, with the exception of the unmodified nonapeptide PyroGlu-Ala-Lys-Ser-Gln-Gly-Gly-Ser-Asn.

The invention is also concerned with the processes for the synthesis of these compounds, including therein the unmodified PyroGlu-Ala-Lys-Ser-Gln-Gly-Gly-Ser-Asn nonapeptide.

The expression "modified amino acid" is understood to signify that the amino acid in question is replaced by its optical antipode or by another amino acid or is even protected by a temporary protective group which is used in the synthesis of the peptides according to the invention.

As replacement or substitution amino acids for the modified amino acids, it is possible to mention, as nonlimiting examples: Ala, Cyano-Ala, Asn, Thio-Asn, Asp, D-Lys, Orn, Lys ($N^6$-acetyl), Glu, D-Gln, Glu($\gamma$-cyano), Glu($\gamma$-CS-NH$_2$), the 2-aminohexanoyl, 2,6-diaminohexynoyl and 2,6-diaminohexenoyl radicals, D-Ser, N-methyl-Ser, Thr, Sar, <Aad, $\beta$-Ala-NH$_2$, Asn-NH$_2$, Arg, Cys(S-CONH$_2$), Har, Hep, Leu, Met(O), Nva and Pro.

As temporary protective groups or groups for activating the carboxyls of the amino acids, the following may be mentioned as nonlimiting examples: Z, BOC, Mbh, But, OBut, OTcp, ONp, OSu, Ac, Nps and OPcp, the abbreviations of which are hereinafter explained.

The expression "N-terminal sequence" is understood to indicate any partial sequence of the Glx-Ala-Lys-Ser-Gln-Gly-Gly-Ser-Asn sequence of which the first residue of amino acid is "Glx" and the expression "C-terminal sequence" is understood to indicate any partial sequence of the Glx-Ala-Lys-Ser-Gln-Gly-Gly-Ser-Asn sequence, of which the last residue of amino acid is "Asn".

It is accordingly possible to define the compounds of the invention as being the polypeptide compounds of sequence X-Gln-Gly-Gly-Y in which Y represents -Ser-Asn and X represents Ser-, Lys-Ser-, Ala-Lys-Ser-, Glx-Ala-Lys-Ser-; and when X represents Glx-Ala-Lys-Ser-, Y may in addition represent -Ser; as well as their derivatives which comprise 1 or 2 modified amino acids, with the exception of the unmodified compound PyroGlu-Ala-Lys-Ser-Gln-Gly-Gly-Ser-Asn.

The abbreviations now being used for the amino acids, as well as for the temporary protective groups of the reactive functions and the reagents and solvents used for the synthesis of the peptides of the invention are as follows:

For the amino acids:
  PyroGlu=L-pyroglutamic acid,
  Ala=L-alanine,
  D-Ala=D-alanine,
  Lys=L-lysine,
  Ser=L-serine,
  Gln=L-glutamine,
  Asn=L-asparagine,
  Asp=L-aspartic acid,
  Glu=L-glutamic acid,
  Orn=L-ornithine,
  Thr=L-threonine,
  Sar=L-sarcosine <Aad = L-pyro-2-aminoadipic acid, homopyroglutamic acid,
β-Ala-NH₂ = amide of β-alanine
Asn-NH₂ = 1,4-diamide of L-aspartic acid,
Arg = L-arginine,
Cys(S-CONH₂) = S-carbamoyl-L-cystein,
Har = L-homoargine,
Hep = L-heptyline, L-2-aminoheptanoic acid,
Leu = L-leucine,
Met(O) = L-methionine sulphoxide,
Nva = norvaline,
Pro = L-proline.

For the temporary protective groups of the reactive functions:
Z = benzyloxycarbonyl,
BOC = ter-butyloxy carbonyl,
Mbh = 4,4'-dimethoxy benzhydryl,
But = ter-butyl,
OMe = methyl ester,
OBut = ter-butyl ester,
OTcp = 2,4,5-trichlorophenyl ester,
ONp = 4-nitrophenyl ester,
OSu = N-hydroxysuccinimide ester,
Ac = acetyl,
Nps = 2-nitrophenyl sulphenyl,
OPcp = pentachlorophenyl ester Reagents and solvents:
NMM = N-methylmorpholine,
DCHA = dicyclohexylamine,
DMF = dimethylformamide,
THF = tetrahydrofuran,
AcOEt = ethyl acetate,
MeOH = methanol,
ButOH = n-butanol.

The peptides containing from 6 to 8 amino acid residues (hexa-, hepta- or octa-peptides), of which the sequence as regards amino acids corresponds to the C-terminal or N-terminal sequence of the natural polypeptide hormone of structure (I), synthesised in accordance with the invention, are the following:

the hexapeptide: Ser-Gln-Gly-Gly-Ser-Asn (36)
the heptapetide: Lys-Ser-Gln-Gly-Gly-Ser-Asn (37)
the octapeptides: Ala-Lys-Ser-Gln-Gly-Gly-Ser-Asn (38)
PyroGlu-Ala-Lys-Ser-Gln-Gly-Gly-Ser (42)

As examples of peptides which have been synthesised by partially modifying the stucture of the natural polypeptide hormone by replacement of one or of two amino acids of L configuration, either by its optical antipode of D configuration, or by another amino acid of more or less analogous structure, or by the same amino acid protected by a temporary protective group in the function of its lateral chain, it is possible to mention the following, in which the modified amino acid is underlined:

| | |
|---|---|
| PyroGlu—D-Ala—Lys—Ser—Gln—Gly—Gly—Ser—Asn | (47) |
| D-Ala—Lys—Ser—Gln—Gly—Gly—Ser—Asn | (45) |
| PyroGlu—Ala—Lys—Ser—Gln—Gly—Gly—Ser—Asp | (53) |
| PyroGlu—Ala—Lys—Ser—Gln—Gly—Gly—Ala—Asn | (59) |
| PyroGlu—Ala—Lys—Ala—Gln—Gly—Gly—Ser—Asn | (60) |
| Z Gln—Ala—Lys—Ser—Gln—Gly—Gly—Ser—Asn | (34) |
| PyroGlu—Ala—D-Lys—Ser—Gln—Gly—Gly—Ser—Asn | (61) |
| PyroGlu—Ala—Lys($N^6$—acetyl)—Ser—Gln—Gly—Gly—Ser—Asn | (62) |
| PyroGlu—Ala—Orn—Ser—Gln—Gly—Gly—Ser—Asn | (63) |
| PyroGlu—Ala—Lys(N—methyl)Ser—Gln—Gly—Gly—Ser—Asn | (64) |
| PyroGlu—Ala—Lys—Ala—Gln—Gly—Gly—Ser—Asn | (65) |
| PyroGlu—Ala—Lys—D-Ser—Gln—Gly—Gly—Ser—Asn | (66) |
| PyroGlu—Ala—Lys—Thr—Gln—Gly—Gly—Ser—Asn | (67) |
| PyroGlu—Ala—Lys—Ser—Glu—Gly—Gly—Ser—Asn | (68) |
| PyroGlu—Ala—Lys—Ser—Glu(γ—cyano)—Gly—Gly—Ser—Asn | (69) |
| PyroGlu—Ala—Lys—Ser—Glu(γ—CS—NH₂)—Gly—Gly—Ser—Asn | (70) |
| PyroGlu—Ala—Lys—Ser—D-Gln—Gly—Gly—Ser—Asn | (71) |
| PyroGlu—Ala—Lys—Ser—Gln—Ala—Gly—Ser—Asn | (72) |
| PyroGlu—Ala—Lys—Ser—Gln—Gly—Ala—Ser—Asn | (73) |
| PyroGlu—Ala—Lys—Ser—Gln—Ala—Ala—Ser—Asn | (74) |
| PyroGlu—Ala—Lys—Ser—Gln—Sar—Sar—Ser—Asn | (75) |
| PyroGlu—Ala—(2-aminohexanoyl)—Ser—Gln—Gly—Gly—Ser—Asn | (76) |
| PyroGlu—Ala—(2,6-diaminohexynoyl)—Ser—Gln—Gly—Gly—Ser—Asn | (77) |
| PyroGlu—Ala—(2,6-diaminohexenoyl)—Ser—Gln—Gly—Gly—Ser—Asn | (78) |
| PyroGlu—Ala—Lys—Ser—Gln—Gly—Gly—Ser—Gln | (79) |
| PyroGlu—Ala—Lys—Ser—Gln—Gly—Gly—Ser—CyanoAla | (80) |
| PyroGlu—Ala—Lys—Ser—Gln—Gly—Gly—Ser—ThioAsn | (81) |
| Lys($N^6$acetyl)—Ser—Gln—Gly—Gly—Ser—Asn | (82) |
| D-Lys—Ser—Gln—Gly—Gly—Ser—Asn | (83) |
| Orn—Ser—Gln—Gly—Gly—Ser—Asn | (84) |
| Nα Z.Lys—Ser—Gln—Gly—Gly—Ser—Asn | (85) |
| PyroGlu—Ala—Lys—Ser—Gln—Gly—Gly—Ser—β—Ala—NH₂ | (86) |
| Hep—Ser—Gln—Gly—Gly—Ser—Asn | (87) |
| Lys—Ser—Gln—D-Ala—Gly—Ser—Asn | (88) |
| PyroGlu—Ala—Lys—Ser—Gln—D-Ala—Ala—Gly—Ser—Asn | (89) |
| PyroGlu—Ala—Lys—Ser—Gln—Gly—Gly—Ser—D-Asn | (90) |
| PyroGlu—Ala—Hep—Ser—Gln—Gly—Gly—Ser—Asn | (91) |
| PyroGlu—Ala—Lys—Ser—Gln—D-Leu—Gly—Ser—Asn | (92) |
| PyroGlu—Ala—Lys—Ser—Gln—Gly—Gly—Ser—Asn—NH₂ | (93) |
| PyroGlu—Ala—Lys—Ser—Gln—Gly—Gly—Thr—Asn | (94) |
| PyroGlu—Ala—Lys—Ser—Gln—Gly—Gly—D-Ser—Asn | (95) |
| PyroGlu—Ala—Lys—Ser—Asn—Gly—Gly—Ser—Asn | (96) |
| PyroGlu—Ala—Lys—Ser—Nva—Gly—Gly—Ser—Asn | (97) |
| PuroGlu—Ala—Lys—Ser—Cys(S—CONH₂)—Gly—Gly—Ser—Asn | (98) |
| PyroGlu—Ala—Lys—Ser—Met(O)—Gly—Gly—Ser—Asn | (99) |
| PyroGlu—Ala—Lys—Ser—Gln—Gly—D-Ala—Ser—Asn | (100) |
| PyroGlu—Ala—Lys—Ser—Gln—Gly—Sar—Ser—Asn | (101) |

| | |
|---|---|
| PyroGlu—Ala—Lys—Ser—Gln—Gly—D-Leu—Ser—Asn | (102) |
| PyroGlu—Ala—Lys—Ser—Gln—Gly—Gly—Gly—Ser—Asn | (103) |
| PyroGlu—Ala—Lys—Ser—Gln—Gly—Ser—Asn | (104) |
| Z—Ala—Lys—Ser—Gln—Gly—Gly—Ser—Asn | (105) |
| D-PyroGlu—Ala—Lys—Ser—Gln—Gly—Gly—Ser—Asn | (106) |
| D-Gln—Ala—Lys—Ser—Gln—Gly—Gly—Ser—Asn | (107) |
| Cys(S—CONH$_2$)—Ala—Lys—Ser—Gln—Gly—Gly—Ser—Asn | (108) |
| Pro—Ala—Lys—Ser—Gln—Gly—Gly—Ser—Asn | (109) |
| <Aad—Ala—Lys—Ser—Gln—Gly—Gly—Ser—Asn | (110) |
| PyroGlu—Ala—Arg—Ser—Gln—Gly—Gly—Ser—Asn | (111) |
| PyroGlu—Ala—Har—Ser—Gln—Gly—Gly—Ser—Asn | (112) |
| PyroGlu—Ala—Lys(N$^6$—acetyl)—Ser—Gln—D-Ala—Gly—Ser—Asn | (113) |
| PyroGlu—Ala—D-Lys(N$^6$—acetyl)—Ser—Gln—Gly—Gly—Ser—Asn | (114) |
| PyroGlu—Ala—Lys(N$^6$—acetyl)—Ser—Gln—Gly—Gly—Ser—D-Asn | (115) |
| Ac—Ala—Lys—Ser—Gln—Gly—Gly—Ser—Asn | (116) |

The compounds (103) and (104) comply with the general definition, with the supplementary condition relative to the modification of the amino acids, according to which it is possible either to add an amino acid or to withdraw an amino acid from the sequence.

SYNTHESIS OF THE SERIC THYMIC FACTOR (STF) AND ITS DERIVATIVES

The synthesis of the two forms of the STF:

PyroGlu-Ala-Lys-Ser-Gln-Gly-Gly-Ser-Asn (I)

Gln-Ala-Lys-Ser-Gln-Gly-Gly-Ser-Asn (II)

is effected in accordance with the invention by different procedures. In a first procedure, there is used a derivative of the glutamine protected on its γ-amide function by the 4,4'-dimethoxybenzhydryl (Mbh) group, while in a second procedure, the synthesis is effected without the protection of the γ-amide group of the glutamine residues.

Using the first and the second procedures, the protected C-terminal dipeptide is respectively coupled to the protected tetrapeptide Ser-Gln-Gly-Gly and to the protected hexapeptide Ala-Lys-Ser-Gln-Gly-Gly.

Thus, the preparation of the polypeptides of sequence

X-Gln-Gly-Gly-Y, in which Y represents -Ser-Asn and X represents Ser- or Ala-Lys-Ser-, is effected by coupling the protected dipeptide Ser-Asn with the protected peptide X-Gln-Gly-Gly and by subsequent possible elimination of the protective groups.

Using the second procedure, it is thus the octapeptide Ala-Lys-Ser-Gln-Gly-Gly-Ser-Asn which is obtained, whereas using the first procedure, the same octapeptide is prepared from the hexapeptide Ser-Gln-Gly-Gly-Ser-Asn, passing by way of the heptapeptide Lys-Ser-Gln-Gly-Gly-Ser-Asn.

The octapeptide Ala-Lys-Ser-Gln-Gly-Gly-Ser-Asn then makes it possible to prepare the two forms of the STF by coupling of the first residue PyroGlu or Gln.

The process used for the coupling of the PyroGlu residue on the sequence Ala-Lys-Ser-Gln-Gly-Gly-Y is the same for the possible different significations of Y, namely, -Ser, and -Ser-Asn, and the possible significations which are derived therefrom by modification of an amino acid, for example for -Ser-Asp, -Ala-Asn.

This coupling is achieved in advantageous manner by means of the PyroGlu-OTcp derivative on the Ala-Lys-Ser-Gln-Gly-Gly-Y sequence, in which certain amino acids are possibly protected in their function of the side chain.

Description of the Stages of the Synthesis of the STF by the First Procedure (A$_1$) Synthesis of the protected C-terminal dipeptide: Z-Ser(But)-Asn-OBut (1), by coupling of the Z-Ser(But) (obtained according to Fluka-Buchs in the form of the DCHA salt) and of the Asn-OBut (prepared according to E. Schnabel and H. Schüssler, Liebigs Al, Chem, 1965, 686, page 229), transformed thereafter into acetate of Ser(But)-Asn-OBut (2) by selective elimination of the temporary protective grouping.

(B$_1$) Synthesis of the dipeptide Z-Gly-Gly-OMe (3), transformed subsequently into Gly-Gly-OMe (4) acetate, by elimination of the Z grouping.

(C$_1$) Synthesis of the tripeptide derivative: Z-Gln(Mbh)-Gly-Gly-OMe (5) by coupling of the derivative Z-Gln(Mbh), (obtained according to W. Köning and R. Geiger, Chem. Ber, 1970, 103, page 2041), with the previously obtained derivative Gly-Gly-OMe (4), and transformation of the tripeptide derivative (5) into its acetate (6).

(D$_1$) Synthesis of the tetrapeptide derivative:

Z-Ser(But)-Gln(Mbh)-Gly-Gly-OMe (7)

by coupling of the Z-Ser(But) derivative (obtained in the form of Z-Ser(But)-DCHA by Fluka, Buchs) with the tripeptide derivative (6).

(E$_1$) Preparation of the derivative Z-Ser(But)-Gln(Mnh)-Gly-Gly-OH (8) by saponification of the derivative (7).

(F$_1$) Synthesis of the hexapeptide derivative:

Z-Ser(But)-Gln(Mbh)-Gly-Gly-Ser(But)-Asn-OBut (9)

by coupling of the C-terminal dipeptide derivative (2) and the tetrapeptide derivative (8). Transformation of the hexapeptide derivative (9) into its acetate (10) by selective elimination of the Z grouping.

(G$_1$) Synthesis of the heptapeptide derivative:

Z-Lys(BOC)-Ser(But)-Gln(Mbh)-Gly-Gly-Ser(But)-Asn-OBut (11)

by coupling of the Z-Lys(BOC) derivative (obtained in the form of Z-Lys(BOC)-DCHA, according to Fluka, Buchs) and the hexapeptide derivative (10). Transformation of the heptapeptide derivative (11) into its acetate (12) by selective elimination of the grouping Z.

(H$_1$) Synthesis of the octapeptide derivative:

Z-Ala-Lys(BOC)-Ser(But)-Gln(Mbh)-Gly-Gly-Ser(But)-Asn-OBut (13)

by coupling of the Z-Ala derivative and the heptapeptide derivative (12). Transformation of the octapeptide derivative (13) into its acetate (14) by elimination of the Z group.

($I_1$) Synthesis of the nonapeptide derivative:

PyroGlu-Ala-Lys(BOC)-Ser(But)-Gln(Mbh)-Gly-Gly-Ser(But)-Asn-OBut (15)

by coupling of the PyroGlu-OTcp derivative (prepared according to J. C. Anderson, M. A. Barton, D. M. Hardy, G. W. Kenner, J. Preston and R. C. Sheppard, J. Chem. Soc. C. 1967, page 108), and the octapeptide derivative (14).

($J_1$) Obtaining the free nonapeptide:

PyroGlu-Ala-Lys-Ser-Gln-Gly-Gly-Ser-Asn (16)

by elimination of all the temporary protective groups in a single step. The free nonapeptide as thus obtained corresponds to the structure (I) of the STF.

($K_1$) Synthesis of the nonapeptide derivative:

Z-Gln(Mbh)-Ala-Lys(BOC)-Ser(But)-Gln(Mbh)-Gly-Gly-Ser(But)-Asn-Obut (17)

by coupling of the Z-Gln(Mbh) derivative (obtained according to W. Köning and R. Geiger, Chem. Ber. 1970, page 2041), and that of the previously obtained octapeptide derivative (14) (see paragraph $H_1$).

($L_1$) Obtaining of the free nonapeptide:

Gln-Ala-Lys-Ser-Gln-Gly-Gly-Ser-Asn (18)

by elimination, firstly of all the temporary protective groups of the functions of the side chain of the amino acids and that of the C-terminal carboxyl, and then of the Z grouping of the N-terminal amine function. The free nonapeptide (18) corresponds to the structure (II) of the STF.

Description of the Stages of the Synthesis of the STF by the Second Procedure ($A_2$) Synthesis of the tripeptide derivative: BOC-Gln-Gly-Gly-OMe (19) by coupling of the BOC-Gln-ONp derivative (obtained by Serva, Heidelberg) and the previously obtained derivative Gly-Gly-OMe (4) (see paragraph ($B_1$). Transformation of the derivative (19) into its trifluoracetate (20) by elimination of the BOC group.

($B_2$) Synthesis of the tetrapeptide derivative:

Z-Ser(But)-Gln-Gly-Gly-OMe (21)

by coupling of the Z-Ser(But) derivative and the derivative (20) Gln-Gly-Gly-OMe. Transformation of the tetrapeptide derivative (21) into its acetate (22) by elimination of the Z group.

($C_2$) Synthesis of the pentapeptide derivative:

Z-Lys(BOC)-Ser(But)-Gln-Gly-Gly-OMe) (23)

by coupling of the derivative Z-Lys(BOC) and the tetrapeptide derivative (22). Transformation of the derivative (23) into its acetate (24).

($D_2$) Synthesis of the hexapeptide derivative:

Z-Ala-Lys(BOC)-Ser(But)-Gln-Gly-Gly-OMe (25)

by coupling of the Z-Ala derivative and the pentapeptide derivative (24).

($E_2$) Preparation of the derivative

Z-Ala-Lys(BOC)-Ser-(But)-Gln-Gly-Gly-NHNH$_2$ (26)

by hydrazinolysis of the methyl ester of the preceding derivative (25).

($F_2$) Synthesis of the octapeptide derivative:

Z-Ala-Lys(BOC)-Ser(But)-Gln-Gly-Gly-Ser(But)-Asn-OBut (27)

by coupling the azide Z-Ala-Lys(BOC)-Ser(But)-Gln-Gly-Gly-N$_3$ obtained from the derivative (26) and the Ser(But)-Asn-OBut derivative (2) (see paragraph $A_1$). Transformation of the octapeptide derivative (27) into its acetate (28) by elimination of the Z grouping.

($G_2$) Synthesis of the nonapeptide derivative:

PyroGlu-Ala-Lys(BOC)-Ser(But)-Gln-Gly-Gly-Ser(But)-Asn-OBut (29)

by coupling of the PyroGlu-O-Tcp derivative (prepared according to J. C. Anderson, M. A. Barton, O. M. Hardy, G. W. Kenner, J. Preston and R. C. Sheppard, J. Chem. Soc. C. 1967, page 108) and the octapeptide derivative (28).

($H_2$) Obtaining the free nonapeptide:

PyroGlu-Ala-Lys-Ser-Gln-Gly-Gly-Ser-Asn (30)

by elimination in a single step of the temporary protective groups. The free nonapeptide (30) as thus obtained is identical with the nonapeptide (16) as previously obtained by the first procedure (see paragraph $J_1$) and corresponds to the structure (I) of the STF.

($I_2$) Synthesis of the nonapeptide derivative:

BOC-Gln-Ala-Lys(BOC)-Ser(But)-Gln-Gly-Gly-Ser(But)-Asn-OBut (31)

by coupling of the BOC-Gln-ONp derivative (obtained by Serva, Heidelberg) and the octapeptide derivative (27) (see paragraph $F_2$).

($J_2$) Obtaining the free nonapeptide:

Gln-Ala-Lys-Ser-Gln-Gly-Gly-Ser-Asn (32)

by elimination in a single step of the temporary protective groupings. The nonapeptide as thus obtained is identical with the nonapeptide (18) peviously prepared by the first procedure (see paragraph $L_1$) and corresponds to the structure (II) of the STF.

($K_2$) Synthesis of the nonapeptide derivative:

Z-Gln-Ala-Lys(BOC)-Ser(But)-Gln-Gly-Gly-Ser(But)-Asn-OBut (33)

by coupling of the Z-Gln-OSu derivative (prepared according to J. Beacham, J. Dupuis, G. Finn, F. M. Storey, H. T. Yanaihara, C. Yanaihara and K. Hofmann, J. Amer, Chem. Soc. 1971, 93, page 5526) and the octapeptide derivative (28) (see paragraph $F_2$).

($L_2$) Obtaining of the nonapeptide derivative:

Z-Gln-Ala-Lys-Ser-Gln-Gly-Gly-Ser-Asn (34)

by elimination of the temporary protective groupings of the functions of the side chain of the amino acids and that of the C-terminal carboxyl of the derivative (33).

(M₂) Obtaining the free nonapeptide:

Gln-Ala-Lys-Ser-Gln-Gly-Gly-Ser-Asn (35)

by elimination of all the temporary protective groupings of the nonapeptide derivative (33). This nonapeptide is identical with the nonapeptide (18) obtained by the first procedure (see paragraph L₁).

Description of the Stages in the Synthesis of the Peptide Fragments of the STF and the "Structural Analogues" of this Factor (A₃) Obtaining the free hexapeptide:

Ser-Gln-Gly-Gly-Ser-Asn (36)

by elimination of the temporary protective groupings of the hexapeptide derivative Z-Ser(But)-Gln(Mbh)-Gly-Gly-Ser(But)-Asn-OBut (9), synthesised by the first procedure (see paragraph F₁).

(B₃) Obtaining of the free heptapeptide:

Lys-Ser-Gln-Gly-Gly-Ser-Asn (37)

by elimination of the temporary protective groupings of the heptapeptide derivative Z-Lys(BOC)-Ser(But)-Gln(Mbh)-Gly-Gly-Ser(But)-Asn-OBut (11) synthesised by the first procedure (see paragraph G₁).

(C₃) Obtaining of the free octapeptide:

Ala-Lys-Ser-Gln-Gly-Gly-Ser-Asn (38), by elimination of the temporary protective groupings of the corresponding octapeptide derivatives (13) and (27), respectively synthesised in accordance with the first procedure and the second procedure (see paragraphs H₁ and F₂). This same free octapeptide has been obtained by the action of the pyroglutamyl-aminopeptidase enzyme (obtained at Boehringer, Mannheim) on the synthetic nonapeptide pyro-Glu-Ala-Lys-Ser-Gln-Gly-Gly-Ser-Asn and separation of the products from enzymatic hydrolysis by preparative rheophoresis on paper.

(D₃) Synthesis of the heptapeptide derivative:

Z-Ala-Lys(BOC)-Ser(But)-Gln-Gly-Gly-Ser(But)-OBut (39)

by coupling of the azide derivative of the hexapeptide Z-Ala-Lys(BOC)-Ser(But)-Gln-Gly-Gly-NHNH₂ (26) obtained by the second procedure (see paragraph E₂) and the derivative: Ser(But)-OBut (prepared according to E. Schroeder, Liebigs. Ann. Chem. 1963, 127, page 670).

Transformation of the hexapeptide derivative (39) into its acetate (40) by elimination of the group Z.

(E₃) Synthesis of the octapeptide derivative:

PyroGlu-Ala-Lys(BOC)-Ser(But)-Gln-Gly-Gly-Ser(But)-OBut (41)

by coupling of the PyroGlu-OTcp (see paragraph I₁) and the heptapeptide derivative (40).

(F₃) Obtaining of the free octapeptide:

PyroGlu-Ala-Lys-Ser-Gln-Gly-Gly-Ser (42)

by elimination of the temporary protective groupings of the octapeptide derivative (41).

(G₃) Synthesis of the octapeptide derivative:

Z-D-Ala-Lys(BOD)-Ser(But)-Gln(Mbh)-Gly-Gly-Ser(But)-Asn-OBut (43)

by coupling of the Z-D-Ala derivative (prepared according to M. Bergmann and L. Zervas, Ber. 1932, 65, page 1192) and the heptapeptide derivative:

Lys(BOC)-Ser(But)-Gln(Mbh)-Gly-Gly-Ser(But)-Asn-OBut (12)

prepared by the first procedure (see paragraph G₁). Transformation of the octapeptide derivative (43) into its acetate (44) by elimination of the Z group.

(H₃) Obtaining the free octapeptide:

D-Ala-Lys-Ser-Gln-Gly-Gly-Ser-Asn (45)

by elimination of the temporary protective groups of the octapeptide derivative (43).

(I₃) Synthesis of the nonapeptide derivative:

PyroGlu-D-Ala-Lys(BOC)-Ser(But)-Gln(Mbh)-Gly-Gly-Ser(But)-Asn-OBut (46)

by coupling of the PyroGlu-OTcp derivative (see paragraph I₁) and the previously obtained octapeptide derivative D-Ala-Lys(BOC)-Ser(But)-Gln(Mbh)-Gly-Gly-Ser(But)-Asn-OBut (43).

(J₃) Obtaining the free nonapeptide:

PyroGlu-D-Ala-Lys-Ser-Gln-Gly-Gly-Ser-Asn (47)

by elimination of the temporary protective groupings.

(K₃) Synthesis of the dipeptide derivative:
Z-Ser(But)-Asp-(OBut)-OBut (48)

obtained by coupling of the Z-Ser(But) (obtained according to Fluka, Buchs) and the Asp-di(OBut) (obtained according to Fluka in the form of a dibenzene sulphimide salt). Transformation of the dipeptide derivative (48) and its acetate (49) by elimination of the Z group.

(L₃) Synthesis of the octapeptide derivative:

Z-Ala-Lys(BOC)-Ser(But)-Gln-Gly-Gly-Ser(But)-Asp-di(OBut) (50)

obtained by coupling the azide of the hexapeptide hydrazide (26) (see paragraph 2) and the previously obtained dipeptide derivative (49). Transformation of the octapeptide derivative (50) into its acetate (51) by elimination of the Z group.

(M₃) Synthesis of the nonapeptide derivative:

PyroGlu-Ala-Lys(BOC)-Ser(But)-Gln-Gly-Gly-Ser(But)-Asp-di(Obut) (52), obtained by coupling the PyroGlu-OTcp derivative (see paragraph I₁) and the previously prepared octapeptide derivative (51).

(N₃) Obtaining the free nonapeptide:

Pyro-Glu-Ala-Lys-Ser-Gln-Gly-Gly-Ser-Asp (53)

by elimination of the temporary protective groupings.

(O₃) Synthesis of the dipeptide derivative:

Z-Ala-Asn-OBut (54)

by coupling of the Z-Ala derivative (prepared according to M. Bergmann and L. Zervas, Ber. 1932, 65, page 1192) and the Asn-OBut derivative (see paragraph A₁). Transformation of the dipeptide derivative (54) into its acetate (55) by elimination of the Z group.

(P₃) Synthesis of the octapeptide derivative:

Z-Ala-Lys(BOC)-Ser(But)-Gln-Gly-Gly-Ala-Asn-OBut (56)

by coupling the azide of the hexapeptide derivative Z-Ala-Lys(BOC)-Ser(But)-Gln-Gly-Gly-NHNH₂ (26) (see paragraph E₂) and the previously prepared dipeptide derivative (55). Transformation of the octapeptide derivative (56) into its acetate (57) by elimination of the Z group.

(Q₃) Synthesis of the nonapeptide derivative

PyroGlu-Ala-Lys(BOC)-Ser(But)-Gln-Gly-Gly-Ala-Asn-OBut (58)

obtained by coupling the Pyro-Glu OTcp derivative (see paragraph I₁) and the previously prepared derivative (57).

(R₃) Obtaining the free nonapeptide:

Pyro-Glu-Ala-Lys-Gln-Gly-Gly-Ala-Asn (59)

by elimination of the temporary protective groupings of the nonapeptide derivative (58).

The synthesis of the peptide compounds according to the invention will be best understood with the assistance of the following examples which are given purely by way of illustration and without any limiting effect as regards the means being used in the invention.

In these examples, the abbreviation TFC indicates thin film chromatography and the abbreviations which are used for the mixtures of solvents are as follows:
A: ethyl acetate/methanol 5:1 (v/v)
B: acetonitrile/benzene 1:1 (v/v)
C: n-butanol/acetic acid/water 3:1:1 (v/v/v)
D: n-butanol/pyridine/acetic acid/H₂O 60:40:12:49 (v/v/v)
E: water-saturated n-butanol
F: chloroform/methanol 10:1 (v/v)
G: methanol/chloroform/concentrated NH₄OH 2:2:1 (v/v/v)
M: N-ammonium acetate/ethanol 3:7 (v/v)
I: chloroform/methanol 3:1 (v/v)
J: ethyl acetate/methanol 2:1 (v/v).

EXAMPLE 1

Preparation of the nonapeptide, PyroGlu-Ala-Lys-Ser-Gln-Gly-Gly-Ser-Asn

Step (a) Preparation of the acetate of Gly-Gly.OMe (4)

To 20.92 g of Z.Gly OH, a commercial product marketed by the firm FLUKA, in solution in 50 ml of DMF, are added 14 ml of triethylamine, while cooling to −20° C. and thereafter 9.54 ml of ethyl chlorocarbonate, marketed by FLUKA. After stirring for 5 minutes at −20° C., there are added 12.56 g of glycine methylester hydrochloride (sold by FLUKA) dissolved in 250 ml of DMF, and then 14 ml of triethylamine. The mixture is left overnight at ambient temperature while stirring.

The insoluble portion is filtered and the solvent is evaporated under the vacuum of the bladed pump. The residue is extracted with 100 ml of ethyl acetate and the solution is washed in succession with 20 ml of a normal solution of KHSO₄, 20 ml of water, 20 ml of KHCO₃ solution and 2×20 ml of water. After drying over MgSO₄, the solvent is evaporated under the vacuum of a water-jet pump. The product as obtained is crystallised in the mixture of AcOEt/petroleum ether between hot and cold.

In this way, 22.4 g of Z.Gly-Gly.OMe (3) (yield 80%) are obtained with a melting point of 67°–68° C. By thin-film chromatography using silica gel in the mixture of solvents J, the product is homogeneous and it is used directly for the following step.

To 8.9 g of the Z.Gly-Gly.OMe (3) as thus obtained, in solution in 400 ml of methanol containing 8 ml of acetic acid, 8 ml of water and 0.9 g of 5% Pd/C, is passed a stream of hydrogen for 4 hours. The catalyst is filtered on Celite and sintered glass and the solvents are evaporated under the vacuum of the water-jet pump. The residue is alternately taken up in benzene and methanol and finally in ether. By triturating the residue in ether, after evaporation of the solvents, the product is solidified. By recrystallisation from the mixture of methanol/ether, there are obtained 5.6 g of Gly-Gly.OMe (4) acetate, in the form of needles (yield 85%), m.p.=95°–98° C. By thin-film chromatography, using silica gel, in the mixture of solvents C, the product is homogeneous.

Step (b) Preparation of the acetate of Gln(Mbh)-Gly-Gly.OMe (6)

To 7.4 g of Z.Gln(Mbh) [prepared by the process described by W. Köning and R. Geiger, Chem. Ber. 103, (1970), 2041] in solution in 100 ml of DMF, cooled to −20° C., are added 1.7 ml of NMM and 1.4 ml of ethyl chlorocarbonate (marketed by the company entitled FLUKA). After 5 minutes, there are added 3.29 g of acetate of Gly-Gly.OMe (4), dissolved in 100 ml of DMF containing 2 ml of NMM. After being left for 30 minutes in the cold, the temperature is allowed to return to ambient temperature overnight. The solvent is evaporated under the vacuum of the bladed pump to 50 ml and filtering takes place. By slowly adding water to the filtrate and by stirring, the precipitation of the tripeptide Z.Gln(Mbh)-Gly-Gly.OMe (5) is obtained in the form of white powder. The precipitate is filtered and washed with 2×100 ml of a normal solution of KHCO₃, with 2×100 ml of water, with 2×100 ml of KHSO₄, with 2×100 ml of water and then with 2×100 ml of ethyl acetate and then with ether. After drying on a drier, there are obtained 8.6 g of Z.Gln(Mbh)-Gly-Gly.OMe (5) (yield 90%). A very small amount of product is dissolved in AcOEt. Recrystallisation takes place from the mixture of DMF/H₂O, m.p.=189°–191° C., $[\alpha]_D = +1.85°$ (C=1, DMF). Homogeneous product by thin-film chromatography using silica gel in the mixtures A and B. The product is used directly for the following step.

To 8.3 g of the Z.Gln(Mbh)-Gly-Gly-OMe (5) as thus obtained, in solution in 500 ml of hot methanol containing 5 ml of CH₃COOH, 5 ml of water and 1 g of 5% Pd/C, is passed a stream of hydrogen until there is no longer any initial product (shown by thin-film chromatography), this requiring about 6 hours of hydrogenolysis. The catalyst is filtered in Celite and sintered glass and rinsed with MeOH. The filtrate is evaporated under the vacuum of the water-jet pump and is taken up several times with MeOH, which is then evaporated. When the product is quite dry, it is caused to dissolve in 50 ml of methanol and it is precipitated with ether. The acetate of Gln(Mbh)-Gly-Gly.OMe (6) is obtained with a yield of 90%, in the form of white powder. The product is directly used for the following step.

Step (c) Preparation of the Z.Ser(But)-Gln(Mbh)-Gly-Gly.OH (8)

To 2.95 g of Z.Ser(But) (product marketed by the company entitled FLUKA), in solution in 100 ml of DMF containing 1.1 ml of NMM and 1 ml of ethyl chlorocarbonate (marketed by the company entitled FLUKA), are added after cooling 5.6 g of acetate of Gln(Mbh)-Gly-Gly.OMe (6) in solution in 50 ml of DMF containing 1.2 ml of NMM.

The sequence of the operations is identical with that previously used for isolating the tripeptide Z.Gln(Mbh)-Gly-Gly.OMe.

6.5 g of Z.Ser(But)-Gln(Mbh)-Gly-Gly.OMe (7) (yield 85%), melting point=199°-202° C. with decomposition $[\alpha]_D = +3.2°$ (C=1, DMF). The product is homogeneous by chromatography, in the mixtures A and B, and it is used directly for the following step.

To 5 g of Z.Ser(But)-Gln(Mbh)-Gly-Gly.OMe (8) as thus obtained, in solution in 350 ml of vigorously stirred 90% MeOH are added 10 ml of the normal solution of NaOH. The cloudy solution gradually clears. The saponification is terminated after 2 hours. 1000 ml of water are added and acidification is effected with CH$_3$COOH. A solvated precipitate is obtained, after having been left for 2 hours in the cold. The precipitate is filtered and it is washed with water. The product is suspended in 300 ml of AcOEt and filtered. Rinsing is carried out several times with ether and a first precipitate is obtained which consists of 3.4 g of Z.Ser(But)-Gln(Mbh)-Gly-Gly.OH (8). After having concentrated the filtrate, a second precipitate of 0.8 g is obtained. The two fractions are identical (yield 85%).

Recrystallisation from the mixture of MeOH/ether (solvated product). M.p.=170°-172° C., $[\alpha]_D = +2.6°$ (C=1, DMF). Homogeneous product by chromatography in the mixtures C and D.

Step (d) Preparation of the Z.Ser(But)-Gln(Mbh)-Gly-Gly-Ser(But)-Asn.OBut (9)

1. Preparation of the Dipeptide Fragment Ser(But)-Asn OBut (2)

To 2.95 g of commercial Z.Ser(But), marketed by the company entitled FLUKA, in solution in 50 ml of THF and cooled to −15° C. or −20° C., are added 1 ml of ethyl chlorocarbonate and 1.1 ml of NMM, marketed by the said firm FLUKA. After 15 minutes, 2.6 g of acetate of Asn.OBut [prepared by the process described by E. Schnabel and H. Schussler, Liebigs Ann. Chem. 685, (1965), 229] in solution in 50 ml of THF, containing 2 ml of NMM, are added. After 30 minutes in the cold, the mixture is left for 16 hours at ambient temperature. The solvent is evaporated with the aid of a rotary evaporator under the vacuum of the water-jet pump. The residue is extracted with 100 ml of AcOEt and the organic solution is washed successively with 20 ml of a normal solution of KHSO$_4$, 20 ml of water, 20 ml of a normal solution of KHCO$_3$ and 2×20 ml of water. After drying over MgSO$_4$, the solvent is evaporated with the assistance of a rotary evaporator under the vacuum of the water-jet pump. A colourless oil is obtained, which is solidified by trituration with petroleum ether.

In this way, 4.2 g of protected dipeptide: Z.Ser(But)-Asn.OBut (1), are obtained. After recrystallization from the mixture of AcOEt/petroleum ether, the physical constants of this product are: m.p.=117°-119° C., $[\alpha]_D = +2.0$ (C=1, DMF). By thin-film chromatography, using silica gel, in the mixtures of the solvents A and B, this product is homogeneous. To 4 g of the Z.Ser(But)-Asn.OBut as thus obtained, in solution in 60 ml of MeOH, are added 2 ml of water, 2 ml of CH$_3$COOH and 0.4 g of 5% Pd/C. Hydrogenolysis is carried out until the initial product disappears (about 4 hours). Filtration takes place and concentration is effected with a rotary evaporator, the substance is taken up several times with methanol and concentrated until a dry product is obtained. It is dried with a drier. Quantitative yield of the acetate of Ser(But)-Asn.OBut (2).

By thin-film chromatography on silica gel in the mixtures of the solvents C and E, the product as obtained is homogeneous and it is directly used for the synthesis of the hexapeptide Ser-Gln-Gly-Gly-Ser-Asn.

2. Preparation of the Hexapeptide Fragment (9)

To 1.68 g of the Z.Ser(But)-Gln(Mbh)-Gly-Gly.OH (8) prepared in step (c), in solution in 20 ml of DMF containing 0.25 ml of NMM and 0.28 ml of isobutyl chlorocarbonate (marketed by FLUKA), are added, after cooling for 5 minutes, 0.98 g of acetate of Ser(But)-Asn.OBut (2), the preparation of which is described above (step (d) 1), in solution in 10 ml of DMF containing 0.5 ml of NMM.

The operations which follow are identical with those described in connection with the preparation of the tripeptide Z.Gln(Mbh)-Gly-Gly.OMe (5). 2.07 g of Z.Ser(But)-Gln(Mbh)-Gly-Gly-Ser(But)-Asn.OBut (9) are obtained with a yield of 87%. Recrystallization from DMF/H$_2$O. M.p.=210°-215° C. with decomposition. $[\alpha]_D = -3.2°$ (C=0.75, DMF).

Step (e) Preparation of the acetate of Ser(But)-Gln(Mbh)-Gly-Gly-Ser(But)-Asn.OBut (10)

To 1.74 g of the hexapeptide ester (9) prepared in step (d), in solution in 80 ml of hot MeOH containing 1 ml of water, 0.8 ml of CH$_3$COOH and 0.25 g of 5% Pd/C is supplied a stream of hydrogen until there is no longer any starting product. Thereafter, the operation is carried out as for the product (6), yield 90%. Homogeneous product in the solvents C and E, used without any other purification for the following step.

Step (f) Preparation of Z.Lys(BOC)-Ser(But)-Gln(Mbh)-Gly-Gly-Ser(But)-Asn.OBut (11)

To 0.6 g of Z.Lys(BOC).DCHA, in solution in 10 ml of DMF, are added, after cooling to −20° C., 0.165 ml of NMM and 0.185 ml of isobutyl chlorocarbonate. Thereafter, 1.41 g of the acetate of the hexapeptide (10) as prepared in step (e) in solution in 10 ml of DMF containing 0.20 ml of NMM are added and the operation is carried out as previously in respect of the tripeptide (5). Yield 90%. Recrystallisation from the mixture of MeOH/ether. Homogeneous product in the mixtures C, E and F. M.p.=208°-211° C. with decomposition. $[\alpha]_D = -3.2°$ (C=0.75, DMF).

Step (g) Preparation of the acetate of Lys(BOC)-Ser(But)-Gln(Mbh)-Gly-Gly-Ser(But)-Asn.OBut (12)

Supplied to 1.21 g of the heptapeptide ester (11) prepared in step (f) in solution in 30 ml of MeOH containing 0.3 ml of water, 0.3 ml of $CH_3COOH$ and 0.1 g of 5% Pd/C is a stream of hydrogen and then the procedure is as previously for the product (6). 1.05 (yield 90%) of a product are obtained in the form of a white powder which is used directly for the following step.

Step (h) Preparation of the Z.Ala-Lys(BOC)-Ser(But)-Gln(Mbh)-Gly-Gly-Ser(But)-Asn.OBut (13)

To 0.2 g of Z.Ala (originating from FLUKA) in solution in 10 ml of DMF, containing 0.10 ml of NMM and 0.117 ml of isobutyl chlorocarbonate, are added 1.16 g of the heptapeptide acetate (12) prepared according to step (g) in solution in 10 ml of DMF containing 0.200 ml of NMM and the operation is carried out in the same manner as for the derivative (5). By recrystallization from the mixture of $DMF/H_2O$, there are obtained 0.961 g of homogeneous product in the mixtures of the solvents C, E and F. M.p.=210°–215° C. with decomposition, $[\alpha]_D = -5.4°$ (C=0.5, DMF).

Step (i) Preparation of the acetate of Ala-Lys(BOC)-Ser(But)-Gln(Pbh)-Gly-Gly-Ser(But)-Asn.OBut (14)

This derivative is obtained with a yield of 90%, by operating as previously for the product (6). The product as obtained, homogeneous in the mixtures of the solvents C and E, is used directly for the following step.

Step (j) Preparation of the PyroGlu-Ala-Lys(BOC)-Ser(But)-Gln(Mbh)-Gly-Gly-Ser(But)-Asn-OBut (15)

To 0.162 g of PyroGlu.OTcp (prepared by the process described by J. C. Anderson, M. A. Barton, D. M. Hardy, G. W. Kenner, J. Preston and R. C. Sheppard, J. Chem. Soc., Series C, 1967, page 108), in solution in 10 ml of DMF and after cooling to 0° C., are added 0.65 g of acetate of octapeptide ester (14), prepared in step i, in solution in 10 ml of DMF containing 0.11 ml of NMM. After 1 hour in an iced bath, it is left for 20 hours at ambient temperature. The solvent is evaporated under the vacuum of a bladed pump to half its volume and the product is precipitated by slowly adding water. After filtering the precipitate, it is washed with 20 ml of water, then with 20 ml of ethyl acetate and with 4×20 ml of ether.

The product is obtained in the form of a white powder, with a yield of 70%. Recrystallisation from a mixture of $DMF/H_2O$, M.p.=224°–228° C. with decomposition, $[\alpha]_D = -4.8°$ (C=1.45, DMF). Product homogeneous in the mixtures C, D and E, used directly for the following step.

Step (k), Obtaining the free nonapeptide PyroGlu-ala-Lys-Ser-Gln-Gly-Gly-Ser-Asn (16)

0.10 g of the protected octapeptide ester (14) are dissolved in 5 ml of a mixture of trifluoroacetic acid/anisol (10:1 v/v). After 3 hours, concentration is carried out on a drier and at ambient temperature in the presence of $P_2O_5$ and KOH. The residue is taken up in 30 ml of water and the aqueous solution is extracted with 10 ml of AcOEt and then with 2×10 ml of ether. The product is obtained by lyophilisation of the aqueous phase, with a yield from 80 to 90%. The product as obtained is homogeneous in the mixtures G and H. After 1 hour of migration by electrorheophoresis in a buffering agent of pH 2.3 (formic acid, 0.1 M) on a Whatman No 3 MM filter paper and under a voltage of 1000 volts (15–30 mA), only a single stain positive to ninhydrin is revealed at −3.2 cm.

Analysis as regards amino acids after acid hydrolysis: Asp 1.07; Ser 1.95; Glu 2; Gly 2; Ala 0.92.

EXAMPLE 2

Preparation of the nonapeptide Gln-Ala-Lys-Ser-Gln-Gly-Gly-Ser-Asn (18)

Step (a) Preparation of the Z.Gln(Mbh)-Ala-Lys(BOC)-Ser(But)-Gln(Mbh)-Gly-Gly-Ser(But)-Asn.OBut (17)

To 0.121 g of Z.Gln(Mbh) [prepared by the process described by W. Köning and R. Geiger, Chem. Ber. 103 (1960), 2041] in solution in 10 ml of DMF, after cooling to −20° C., are added 0.027 ml of NMM and 0.031 ml of isobutyl chlorocarbonate. Thereafter, this mixture has added thereto 0.270 g of the octapeptide acetate (14) prepared in step (i) of Example 1, in a cooled solution of 10 ml of DMF containing 0.027 ml of NMM. After 30 minutes in the cold, the mixture is left for 14 hours at ambient temperature. The solvent is evaporated to about 5 ml and 50 ml of water are slowly added, and a fine precipitate is obtained which is filtered and then washed with 2×10 ml of a normal solution of $KHCO_3$, with 2×10 ml of water, with 2×10 ml of normal solution of $KHSO_4$, with 2×10 ml of water and then with 20 ml of AcOEt and with ether. The product as obtained is taken up in hot methanol. The product which remains insoluble is the protected nonapeptide ester. After filtration and rinsing with ether, 0.200 g (yield 50%) of the product are obtained. M.p.=221°–225° C., $[°]_D = -5.8°$ (C=0.6, DMF). Homogeneous in the mixture E.

Step (b) Preparation of the free nonapeptide Gln-Ala-Lys-Ser-Gln-Gly-Gly-Ser-Asn (18)

100 mg of the protected nonapeptide ester (17), prepared in step (a), are dissolved in 5 ml of the trifluoacetic acid/anisol mixture (10:1 v/v). After 3 hours, the mixture is concentrated in a drier under vacuum in the presence of $P_2O_5$ and KOH. The residue is taken up with 20 ml of water and the aqueous solution is washed with 10 ml of AcOEt and with 2×10 ml of ether. The aqueous phase is concentrated to about 1 ml. The aqueous solution of the peptide Z.Gln-Ala-Lys-Ser-Gln-Gly-Gly-Ser-Asn gives a single stain in the mixtures G and H and, by rheophoresis under the same conditions as those previously used for the product (16) in step (k) of Example 1, there is revealed as regards the ninhydrin a single stain which migrates to −2.7 cm in the buffering agent of pH 2.5.

10 ml of MeOH, 0.1 ml of acetic acid and 10 mg of 5% Pd/C are added to this solution and a stream of hydrogen is caused to pass therethrough for 4 hours. The catalyst is filtered and concentration takes place under the vacuum of the water-jet pump. The residue is taken up in 20 ml of water and the aqueous solution is washed with 2×10 ml of ether. The product is obtained by lyophilisation of the aqueous phase. It is homogeneous in the mixtures G and H and, with the rheophoresis under the previously described conditions, gives a single stain which migrates to −5.8 cm at pH 2.5.

Analysis as regards amino acids after total acid hydrolysis: Asp 0.98; Ser 1.62; Glu 1.95; Gly 2.00; Ala 1.02.

EXAMPLE 3

Preparation of the free hexapeptide
Ser-Gln-Gly-Gly-Ser-Asn

This peptide fragment, corresponding to the C-terminal hexapeptide of the thymic factor of the serum, is obtained from the derivative Z.Ser(But)-Gln(Mbh)-Gly-Gly-Ser(But)-Asn.OBut, prepared in step (d) of Example 1, by elimination of the temporary protective groupings, under the conditions previously described in respect of the peptide (16) in step (k) of Example 1. The product obtained is homogeneous in the mixtures G and H.

Analysis as regards amino acids after total acid hydrolysis: Asp 1.02; Ser 1.75; Glu 1.0; Gly 2.00.

EXAMPLE 4

Preparation of the free heptapeptide
Lys-Ser-Gln-Gly-Gly-Ser-Asn

This peptide fragment corresponds to the C-terminal heptapeptide of the thymic factor of the serum. It is obtained from the derivative Z-Lys(BOC)-Ser(But)-Gln(Mbh)-Gly-Gly-Ser(But)-Asn.OBut (11) prepared in step (f) of Example 1, by elimination of the temporary protective groupings under the conditions as previously described for the peptide (16) in step (k) of Example 1. The product obtained is homogeneous in the solvents G and H and, by rheophoresis under the conditions described for the products (16) and (18), gives a single stain which migrates to −6.25 cm at pH 2.5.

Analysis of amino acids after total acid hydrolysis: Asp 1.04; Ser 1.73; Glu 1.03; Gly 2.00.

EXAMPLE 5

Preparation of the Free Octapeptide
Ala-Lys-Ser-Gln-Gly-Gly-Ser-Asn (38)

This fragment corresponds to the C-terminal octapeptide of the thymic factor of the serum. It is obtained like the preceding fragments from the corresponding protected derivative W(13) obtained in step (h) of Example 1. The product thus obtained is homogeneous in the mixtures G and H and, by rheophoresis, gives a single stain which migrates to −4.65 cm at pH 2.5, under the previously described conditions.

Analysis of amino acids after total acid hydrolysis: Asp 1.0; Ser 0.94; Glu 1.02; Gly 2.00; Ala 0.96.

This same free octapeptide may also be obtained by the action of the pyroglutamyl aminopeptidase enzyme of commercial origin on the synthetic nonapeptide PyroGlu-Ala-Lys-Ser-Gln-Gly-Gly-Ser-Asn and separation of the products of enzymatic hydrolysis by preparative rheophoresis on Whatman paper No 3 MM.

EXAMPLE 6

Preparation of the Free Octapeptide
PyroGlu-Ala-Lys-Ser-Gln-Gly-Gly-Ser (42)

This fragment corresponds to the N-terminal octapeptide of the STF. It is obtained by synthesis, in accordance with the following steps:

Step (a) Preparation of the tripeptide derivative
BOC.Gln-Gly-Gly.OMe (19)

To 10.96 g of commercial BOC.Gln.ONp, sold by the company entitled SERVA, in solution in 10 ml of DMF containing 4.18 ml of triethylamine, are added 6.15 g of acetate of Gly-Gly.OMe (4), prepared in step (a) of Example 1. After stirring the mixture overnight at normal temperature, the DMF is evaporated under the vacuum of the bladed pump and the residue is dissolved in 125 ml of water. The aqueous solution is washed four times with ether and then the solution is saturated with NaCl, whereafter the product is extracted by a total amount of 2.5 liters of ethyl acetate. The ethyl acetate solution is evaporated to dryness and the residue is dried on the drier over $H_2SO_4$. After trituration of the residue with ether, 8.65 g (yield 78%) of BOC.Gln-Gly-Gly.OMe are obtained in the form of a hygroscopic powder which is directly used for the following step. The product is homogeneous by thin-film chromatography in the mixture J (MeOH/AcOEt, 1:2).

Step (b) Preparation of the Trifluoroacetate of
Gln-Gly-Gly.OMe (20)

The derivative (20) is prepared from 8.65 g of the derivative (19) prepared in step (a) by the action of 125 ml of 95% trifluoacetic acid at ambient temperature for 15 minutes and evaporation under vacuum of the acid. After trituration in ether, the product is solidified. Recrystallisation is carried out in the mixture of methanol/ethyl acetate. 7.25 g of product (yield 81%) are obtained. Product homogeneous by thin-film chromatography in the mixture C-ButOH/$CH_3COOH$/$H_2O$ (3:1:1). M.p.=165°–167° C., $[\alpha]_D=+13.8°$ (C=1, MeOH).

Step (c) Preparation of the tetrapeptide derivative
Z.Ser(But)-Gln-Gly-Gly.OMe (21)

12.57 g of Z.Ser(But)DCHA (produced by FLUKA) are desalted by using the process of Spagenberg et al. (Hoppe Seyler, Zts. Physiol. Chem. 1971, 352, 655).

To the residue as obtained, dissolved in 100 ml of THF, are added 3.7 ml of triethylamine and, after cooling the solution to −15° C., 2.3 ml of ethyl chlorocarbonate are added. After 5 minutes, there are added 8.54 g of trifluoroacetate of Gln-Gly-Gly.OMe (20) prepared in step (b) and 3.1 ml of triethylamine dissolved beforehand in a mixture of DMF and THF.

The mixture is left while stirring at ambient temperature. After filtering the triethylamine hydrochloride formed, the THF is evaporated under the vacuum of the water-jet pump and then 200 ml of $KHCO_3$, 1 M, are added to the solution which remains. By extraction of the mixture with 1 liter of chloroform, a chloroformic solution is obtained which is washed with water saturated with NaCl, with normal $KHSO_4$ and then with water to the point of neutrality.

After the chloroform solution has been evaporated to dryness, the residue is dried on the drier over $H_2SO_4$. By crystallisation of the residue in the mixture of methanol/ether, the product is homogeneous by thin-film chromatography in the mixture consisting of MeOH 1/AcOET 2. 9.1 g of product are obtained (yield 75%). After recrystallisation from the mixture of DMF/ether, m.p.=163°–167° C., $[\alpha]_D=+3.4°$ (C=1.16, DMF).

Step (d) Preparation of the Acetate of Ser(But)-Gln-Gly-Gly.OMe (22)

3.3 g of Z.Ser(But)-Gln-Gly-Gly.OMe (21) prepared in step c) in solution in 150 ml of MeOH containing 1.5 ml of water and 1.5 ml of $CH_3COOH$, are hydrogenated in the presence of 5% Pd/C for 5 hours. Thereafter, the operation is carried out in the manner as described for the product (6) in step (b) of Example 1. The thoroughly dry product is rinsed several times with ether (yield 2.8 g). Homogeneous product by thin-film chromatography in the mixtures of solvents C and E.

Step (e) Preparation of the derivative Z.Lys(BOC)-Ser(But)-Gln-Gly-Gly.OMe (23)

To a solution of 1.9 g of Z.Lys(BOC) in 30 ml of DMF cooled to $-15°$ C. are added 0.55 ml of NMM and 0.65 ml of isobutyl chlorocarbonate. After 5 minutes, there is added a cold solution in 30 ml of DMF containing 2.4 g of acetate of Ser(But)-Gln-Gly-Gly.OMe (22) prepared in step (d) and 1 ml of NMM. After 30 minutes at $-15°$ C. and one night at ambient temperature, 1 liter of chloroform and 200 ml of normal $KHCO_3$ are added. After stirring, decantation is allowed to occur and the chloroformic layer is separated, this being washed with $2 \times 100$ ml of water. The aqueous phases are re-extracted with 1 liter of chloroform. The organic phases are recombined and they are dried over $MgSO_4$. The chloroformic solution is concentrated under vacuum and the residue is triturated in ether. 2.9 g of a white powder are obtained (yield 75%). The product obtained is homogeneous by thin-film chromatography in the mixtures of solvents E and J. M.p.$=194°-198°$ C. with decomposition, $[\alpha]_D = -1.9°$ (C=2, DMF).

Step (f) Preparation of the Acetate of Lys(BOC)-Ser(But)-Gln-Gly-Gly.OMe (24)

2.9 g of the derivative (23) obtained in step (e) are hydrogenated in the manner as previously described in 50 ml of MeOH, 0.5 ml of $CH_3$-COOH and 0.5 ml of water, in the presence of 50 mg of 5% Pd/C for 5 hours. 2.8 g of a product homogeneous by thin-film chromatography in the solvents C and E are obtained, the product being used directly for the following step.

Step (g) Preparation the Z.Ala-Lys(BOC)-Ser(But)-Gln-Gly-Gly.OMe (25)

To a solution of 0.892 g of Z.Ala in 30 ml of DMF cooled to $-15°$ C. are added 0.522 ml isobutyl chlorocarbonate and 0.44 ml of NMM. After 5 minutes, a solution of 70 ml of DMF is added which contains 2.8 g of the acetate of Lys(BOC)-Ser(But)-Gln-Gly-Gly.OMe (24), prepared in step (f) and 0.8 ml of NMM. After 30 minutes in the cold, the mixture is left for one night at ambient temperature and the solution is concentrated to a volume of 50 ml under the vacuum of the bladed pump. 450 ml of water are then slowly added. The formed precipitate is filtered, washed with water and then with a normal solution of $KHCO_3$, and once again with water. Rinsing is carried out with ether, followed by drying on the drier. 2.7 g (yield 80%) are obtained of a product homogeneous by thin-film chromatography in the solvents F. and J. M.p. $210°-220°$ C. with decomposition, $[\alpha]_D = 1.7°$ (C=2.2, DMF).

Step (h) Preparation of Z.Ala-Lys(BOC)-Ser(But)-Gln-Gly-Gly-NHNH$_2$ (26)

2.3 g of the derivative (25), prepared in step (g), are dissolved in 150 ml of methanol by heating. After cooling, 2.6 ml of 98% hydrazine hydrate are added and the solution is vigorously stirred. It is left for one night at ambient temperature, whereafter it is cooled to $-20°$ C. and the precipitate which is obtained is filtered. This first precipitate is washed with ether. The mother liquors are concentrated: the second precipitate is triturated in ether. The two products as thus obtained are identical: dried under vacuum, using the drier, on $H_2SO_4$, they give 2.2 g of a product which is homogeneous by thin-film chromatography in the mixtures of solvents I and J. M.p.$=191°-195°$ C. with decomposition; $[\alpha]_D = -3.8°$ (C=2.2, DMF).

Step (i) Preparation of the Z.Ala-Lys(BOC)-Ser(But)-Gln-Gly-Gly-Ser(But)-.OBut (39)

To a solution of 0.85 g of the derivative (26) prepared in step (h) in 30 ml of DMF cooled to $-40°$ C. are added 0.63 ml (5 equivalent) of an anhydrous solution of 8-normal HCl/THF and 0.16 ml of isoamyl nitrile. The solution is maintained for 30 minutes while stirring at $-40°$ C. and then there are added 1.4 ml of triethylamine and 0.366 g of the hydrochloride of Ser(But).OBut, prepared according to E. Schroeder (Liebigs Ann. Chem. 1963, 127, page 670). After 1 hour at $-40°$ C., the solution is left in the freezer for 48 hours. Concentration is carried out under the vacuum of the bladed pump to a volume of 10 ml and 200 ml of water are slowly added. After 4 hours in the cold, the precipitate is filtered, this being rinsed with water and then with ether. A white powder is obtained which is homogeneous by thin-film chromatography in the mixtures of solvents E, F and J. Recrystallisation from the mixture of methanol/ether.

M.p.$=225°-230°$ C. with decomposition; $[\alpha]_D = -4.0°$ (C=1, DMF).

Step (j) Preparation of the acetate of Ala-Lys(BOC)-Ser(But)-Gln-Gly-Gly-Ser(But).OBut (40)

This derivative is obtained from 0.50 g of the derivative (39) prepared according to the step (i) under the conditions previously described for the derivatives (22) and (24) (steps d and f). Yield is quantitative. Product homogeneous by thin-film chromatography in the mixtures of solvents C and E, used directly for the following step.

Step (k) Preparation of the PyroGlu-Lys(BOC)-Ser(But)-Gln-Gly-Gly-Ser(But)-.OBut (41)

To a solution of 0.25 g of the product (40), prepared in step (j) in 10 ml of DMF cooled to $0°$ C. is added 0.03 ml of NMM and then, after 5 minutes, 0.088 g of Pyro-Glu.OTop (prepared according to J. C. Anderson et al, J. Chem. Soc. C. 1967, page 108). After 30 minutes in the cold, the solution is left for 18 hours at ambient temperature. The solution is concentrated under vacuum (bladed pump). The residue is triturated in ethyl acetate in the hot state and then in ether. 0.195 g is obtained (yield 70%). Recrystallisation from the methanol/ether mixture: product homogeneous by thin-film chromatography in the mixtures of solvents E, F and J. M.p.=219°-222° C.; $[\alpha]_D = -3.0°$ (C=0.9, DMF).

Step (l) Preparation of the free octapeptide PyroGlu-Ala-Lys-Ser-Gln-Gly-Gly-Ser (42)

0.020 g of the derivative (41) prepared in step k) are dissolved in 5 ml of a mixture of CF$_3$COOH/anisol (10:1 v/v). After 3 hours at ambient temperature, concentration is carried out on a drier under vacuum. The residue is taken up in 40 ml of water. Extraction is effected with 20 ml of ethyl acetate and with 20 ml of ether. The aqueous phase is lyophilised. The product obtained is homogeneous by thin-film chromatography in the mixture of solvents G and H.

By rheophoresis in a buffering substance of pH 2.3 (formic acid 0.1 M) on Whatman paper No. 3 MM and under a voltage of 1000 V (15–30 mA), a single stain is found at −2.9 cm.

Analysis as regards amino acids after total acid hydrolysis: Ser. 1.87; Glu 1.92; Gly 2.00; Ala 1.01.

EXAMPLE 7

Preparation of the Octapeptide Analogue D-Ala-Lys-Ser-Gln-Gly-Gly-Ser-Asn (45)

This structural analogue corresponds to the C-terminal octapeptide (38) as previously described (Example 5), except for the single difference that the L-Ala residue is replaced by the D-Ala residue. It is obtained by synthesis in accordance with the following steps:

Step (a) Preparation of the derivative Z.D-Ala-Lys(BOC)-Ser(But) Gln(Mbh)-Gly-Gly-Ser(But)-Asn.OBut (43)

To a solution of 0.03 g of Z.D-Ala (prepared according to M. Bergmann and L. Zervas, Ber. 1932, 65, 1192), in solution in 1 ml of DMF cooled to −15° C., are added while stirring 0.015 ml of NMM and 0.018 ml of isobutyl chlorocarbonate and then, after 5 minutes, a solution of 0.172 g of the acetate of Lys(BOC)-Ser(But)-Gln(Mbh)-Gly-Gly-Ser(But)-Asn.OBut (12), the preparation of which is described under step (g) of Example 1 and 0.03 ml of NMM in 5 ml of DMF. After 30 minutes at −15° C., the solution is left overnight at ambient temperature. The solution is concentrated to a volume of 1 ml and 20 ml of a 10% citric acid solution are slowly added. A precipitate in the form of a fine powder is established, and this is filtered and then it is rinsed several times with water, and then with a normal solution of KHCO$_3$ and once again with water. It is rinsed several times with ether and dried in the drier under vacuum. 0.165 g of the product in the form of a fine powder are obtained (yield 85%).

Recrystallisation from the methanol/ether mixture.

Product homogeneous by thin-film chromatography in the mixtures of solvents C, E and F; M.p.=211°-215° C. with decomposition; $[\alpha]_D = -3.3°$ (C=0.45, DMF).

Step (b) Preparation of the acetate of D-Ala-Lys(BOC)-Ser(But)-Gln(Mbh)-Gly-Gly-Ser(But)-Asn.OBut (44)

0.11 g of the derivative (43) prepared according to step (a) are hydrogenated under the conditions as previously described in 10 ml of MeOH, 0.1 ml of CH$_3$COOH and 0.1 ml of water and in the presence of 10 ml of 5% Pd/C for 4 hours. A homogeneous product is obtained which is used directly for the following step.

Step (c) Preparation of the free octapeotide D-Ala-Lys-Ser-Gln-Gly-Gly-Ser-Asn (45)

Starting from the derivative (44) prepared according to step (b) the free octapeptide is obtained by operating in accordance with the process as described for obtaining the nonapeptide PyroGlu-Ala-Lys-Ser-Gln-Gly-Gly-Asn (16) in step k) of Example 1.

A product homogeneous with thin-film chromatography in the mixtures G and H is obtained.

By rheophoresis under the same conditions as those previously described for the peptide (42) in step (1) of Example 6, a single stain is obtained which migrates to −4.65 cm.

Analysis as regards amino acids after total acid hydrolysis: Asp 1.02; Ser. 1.77; Glu 1.0; Gly 2.00; Ala 0.91

EXAMPLE 8

Preparation of the Nonapeptide Analogue PyroGlu-D-Ala-Lys-Ser-Gln-Gly-Gly-Ser-Asn (47)

This analogue with a structure corresponding to the nonapeptide (16) of Example 1, having the structure of the seric thymic hormone, with the only difference that the L-Ala residue is replaced by the D-Ala residue. It is obtained by synthesis from the derivarive (44) as previously described (step b) of Example 7, using the following steps:

Step (a) Preparation of the PyroGlu-D.Ala-Lys(BOC)-Ser(But)-Gln(Mbh)-Gly-Gly-Ser(But)-Asn.OBut (46)

To a solution of 0.104 g of acetate of Lys(BOC)-Ser(But)-Gln(Mbh)-Gly-Gly-Ser(But)-Asn.OBut (44) as previously described (step b) in Example 7 in 3 ml of DMF cooled to 0° C. are added 30 μl of NMM and then, after 5 minutes, a solution of 29 mg of PyroGlu-OTcp (prepared according to J. C. Anderson et al, J. Chem. Soc., C, 1967, page 108) in 5 ml of DMF. The solution is left for 24 hours at ambient temperature and then the solution is concentrated to a volume of 1 ml and 20 ml of water are slowly added until a fine precipitate is obtained, which is filtered. Rinsing is carried out with ethyl acetate and ether and 0.078 g (yield 70%) of a product are obtained which is homogeneous by thin-film chromatography in the mixtures of solvents C, D and E.

M.p.=210°-215° C., $[\alpha]_D = -5.0°$ (C=0.4, DMF).

Step (b) Preparation of the free nonapeptide (47)

Starting from the preceding derivative (46), the free nonapeptide is obtained by operating in accordance with the process employed for obtaining the octapeptide (45) and the nonapeptide (16). A product homogeneous by thin-film chromatography in the solvents G and H is obtained. By rheophoresis at pH 2.3, a single stain is disclosed which migrates to −3.2 cm.

Analysis as regards amino acids after total acid hydrolysis: Asp 0.97; Ser. 1.67; Glu 1.84; Gly 2.00; Ala 0.98.

EXAMPLE 9

Preparation of the Analogue of Nonapeptidic Structure, PyroGlu-Ala-Lys-Ser-Gln-Gly-Gly-Ser-Asp (53)

This analogue corresponds to the nonapeptides (16) and (30) having the structure of the seric thymic hormone, with the only difference that the C-terminal L- asparagine (Asn) residue is replaced by the L-aspartic (Asp) residue.

It is obtained by synthesis according to the following steps:

Step (a) Preparation of the derivative Z-Ser(But)-Asp-di.OBut (48)

To a solution of 0.295 g of Z-Ser(But) (produced by FLUKA) in 10 ml of DMF, cooled to −15° C., are added 0.12 ml of NMM and 0.13 ml of isobutyl chlorocarbonate. After 5 minutes, there is added a cold solution of 10 ml of DMF containing 0.54 g of di-tert.butyl aspartate in the form of a dibenzosulphimide salt (produced by FLUKA) and 0.15 ml of NMM. It is left while stirring for 30 minutes in the cold and for one night at ambient temperature. The solution is then concentrated under vacuum and the residue is taken up in 100 ml of ethyl acetate. It is washed with 50 ml of a normal solution of $KHSO_4$, water, the N salt of $KHCO_3$ and once again with water. The organic phase is dried over $MgSO_4$ and then concentrated under vacuum. An oil is obtained which crystallises by addition of petroleum ether. By recrystallisation from the petroleum ether, there is obtained 0.43 g (yield 80%) of a product which is homogeneous by thin-film chromatography in the mixture of ether/petroleum ether 1:1 v/v.

M.p.=83°–85° C.; $[\alpha]_D = -4.9°$ (C:1.25, DMF).

Step (b) Preparation of the Acetate of Ser(But)-Asp-di.OBut (49)

0.26 g of the derivative (48), prepared in accordance with step a), dissolved in 10 ml of methanol containing 0.1 ml of $CH_3COOH$ and 0.1 ml of water, are hydrogenated in the presence of 0.1 g of 5% Pd/C for 2 hours. The acetate of Ser(But)-Asp-di.OBut, obtained with a quantitative yield, is homogeneous by thin-film chromatography in the mixtures of solvents C and E and it is used directly for the following step.

Step (c) Preparation of the Z-Ala-Lys(BOC)-Ser(But)-Gln-Gly Gly-Ser(But)-Asp-di.OBut (50)

To a solution of the Z-Ala-Lys(BOC)-Ser(But)-Gln-Gly-Gly-$NHNH_2$ (26) derivative (obtained according to step h) of example 6) in 10 ml of DMF is added 0.175 ml of an 8 N solution of HCl/THF and cooling takes place to −40° C. 0.045 ml of isoamyl nitrite are then added and the solution is left while stirring at −40° C. for 30 minutes. There is then added a cooled solution of 10 ml of DMF containing 0.18 g of the acetate of Ser(But)-Asp-di.OBut (49) prepared in step (b) and 0.1 ml of triethylamine. The solution is left at −40° C. for 30 minutes and then for 48 hours in a freezer. The solution is then concentrated under vacuum and the residue is triturated in 20 ml of water. The precipitate is filtered and rinsing is effected with ether. The precipitate is taken up in 5 ml of methanol, it is reprecipitated with ether and the powder which is obtained is filtered.

By recrystallisation from methanol between hot and cold, 0.25 g (yield 75%) of a product homogeneous by thin-film chromatography in the mixtures of solvents I and J are obtained.

M.p.=220° C. with decomposition; $[\alpha]_D = -8.0°$ (C=0.6, DMF).

Step (d) Preparation of the Acetate of Ala-Lys(BOC)-Ser(But)-Gln-Gly-Gly-Ser(But)-Asp-di.OBut (51)

The catalytic hydrogenation of 0.15 g of the derivative (50) of the step (c) in 10 ml of methanol containing 0.1 ml of $CH_3COOH$ and 0.1 ml of water and 10 mg of 5% Pd/C provides, after 3 hours, a product which is homogeneous by thin-film chromatography in the solvents C and I, with a quantitative yield. This product is directly used for the following step.

Step (e) Preparation of the PyroGlu-Ala-Lys(BOC)-Ser(But)-Gln-Gly-Gly-Ser(But)-Asp-di.OBut (52)

To a solution of 0.126 g of the preceding derivative (51) dissolved in 4 ml of DMF and cooled to 0° C. are added 0.038 ml of NMM, and then, after 5 minutes, 0.038 g of PyroGlu-O-Tcp (prepared according to J. C. Anderson et al., J. Chem. Soc., C, 1967, page 108). The solution is left for 30 minutes in the cold and then for 24 hours at ambient temperature, whereafter the solution is concentrated under vacuum and the residue is triturated in water, in ethyl acetate and in ether. The precipitate is filtered, which precipitate is dissolved in the minimum of hot methanol, and it is reprecipitated by ether. By recrystallisation in methanol between hot and cold, there are obtained 0.085 g (yield 65%) of a product which is homogeneous in the mixtures of solvents C and I.

M.p.=225° C. with decomposition; $[\alpha]_D = -5.8°$ (C=0.4, DMF).

Step (f) Preparation of PyroGlu-Ala-Lys-Ser-Gln-Gly-Gly-Ser-Asp (53)

0.02 g of the derivative (52) of the step (e) dissolved in 5 ml of a mixture of $CF_3COOH$/anisol 10/1 v/v are left for 3 hours at ambient temperature. The solution is concentrated in a drier and the residue is taken up in 40 ml of water, extracted with 20 ml of ethyl acetate and 20 ml of ether and the aqueous phase is lyophilised. The product as obtained is homogeneous as regards thin-film chromatography in the solvents G and H. By rheophoresis under the conditions as previously described for the peptide (42) in Example 6, a single stain is obtained which migrates to −2.8 cm.

Analysis as regards amino acids after total acid hydrolysis: Asp 1.05; Ser. 1.73; Glu 1.97; Gly 2.00; Ala 1.02.

EXAMPLE 10

Preparation of the Nonapeptide Analogue PyroGlu-Ala-Lys-Ser-Gln-Gly-Gly-Ala-Asn (59)

This analogue corresponds to the nonapeptide having the structure of the seric thymic hormone, with the only difference that the $Ser_8$ residue in the penultimate position, which is replaced by the Ala residue.

It is obtained by synthesis in accordance with the following steps

Step (a) Preparation of the Z-Ala-Asn OBut derivative (54)

0.461 g of Z-Ala (produced by FLUKA) in solution in THF have added thereto 0.23 ml of NMM, followed by cooling to −15° C., whereafter 0.25 ml of isobutyl chlorocarbonate are added. After 5 minutes there is added a solution in THF of the acetate of Asn-OBut (prepared according to E. Schnabel and H. Schüssler, Liebig's Ann. Chem. 1965, 685, 229) and 0.38 ml of NMM. After one night at ambient temperature while stirring, the solvent is evaporated and the residue is taken up in ethyl acetate. The organic solution is washed with a M solution of KHSO$_4$, with water, with a M solution of KHCO$_3$ and once again with water. The organic phase is dried over MgSO$_4$. By evaporation of the ethyl acetate, a residue is obtained which crystallises by addition of petroleum ether. Recrystallisation is carried out in the mixture of ethyl acetate and petroleum ether. 0.635 g (yield 94%) of a product homogeneous in the mixture of solvents A are obtained.

M.p.=156°-158° C.; $[\alpha]_D = -9.0°$ (C=1.13, DMF).

Step (b) Preparation of the Acetate of Ala-Asn.OBut (55)

A solution of 0.25 g of the derivative (54) of the step (a), in 15 ml of methanol, 0.5 ml of CH$_3$COOH and 0.5 ml of water, containing 20 mg of 5% Pd/C, is hydrogenated for 5 hours. Filtration takes place on sintered glass and Celite, followed by evaporation to dryness, and the residue is successively taken up with benzene and methanol. Quantitative yield of a product homogeneous by thin-film chromatography in the mixtures of solvents C and E.

The product obtained is used directly for the following step.

Step (c) Preparation of
Z-Ala-Lys(BOC)-Ser(But)-Gln-Gly-Gly-Ala-Asn OBut (56)

To a solution of 0.28 g of the derivative Z-Ala-Lys(-BOC-Ser(But)-Gln-Gly-Gly-NHNH$_2$ (26) (obtained in step h) of Example 6), in 10 ml of DMF, and after cooling to $-40°$ C., there are added 0.208 ml of an 8 N-solution of HCl/THF, followed by 0.058 ml of isoamyl nitrite. After 30 minutes at $-40°$ C., there are added 0.50 ml of triethylamine and a solution of 0.14 g of Ala-Asn OBut acetate (55) prepared in step (b) in 5 ml of DMF. After 1 hour at $-40°$ C. while stirring, the solution is left for 48 hours in the freezer. The solution is concentrated under vacuum and the residue is triturated in 20 ml of water, then in 20 ml of ethyl acetate and in 30 ml of ether. After filtration, a white powder is obtained which is recrystallised from methanol between hot and cold. The product is homogeneous as regards thin-film chromatography in the mixtures of solvents C and I.

M.p.=210° C. with decomposition; $[\alpha]_D = -12.9°$ (C=0.9, DMF).

Step (d) Preparation of the acetate of
Ala-Lys(BOC)-Ser(But) Gln-Gly-Gly-Ala-Asn-OBut (57)

0.015 g of the derivative (56) of step (c) in solution in 10 ml of methanol, 0.1 ml of CH$_3$COOH and 0.5 ml of water, containing 10 ml of 5% Pd/C, are hydrogenated for 4 hours. A product is obtained with a quantitative yield, which is homogeneous by thin-film chromatography in the mixtures of solvents C and E which are used for the following step.

Step (e) Preparation of
PyroGlu-Ala-Lys(BOC)-Ser(But)-Gln-Gly-Gly-Ala-Asn OBut (58)

To a solution of 0.10 g of the derivative (57) of step (d) in 5 ml of DMF, after cooling to 0° C., are added 0.02 ml of NMM and, after 10 minutes, 0.033 g of Pyro-Glu OTcp (prepared according to J. C. Anderson et al., J. Chem. Soc., C, 1967, page 108). After 24 hours at ambient temperature while stirring, the solvent is evaporated under vacuum and the residue is triturated in hot chloroform. The powder which is obtained is filtered and rinsed with ether. By recrystallisation from the methanol between hot and cold, 0.065 g of a product homogeneous by thin-film chromatography in the mixtures of solvents C and E is obtained.

M.p=210° C. with decomposition; $[\alpha]_D = -13.7°$ (C=0.95, DMF).

Step (f) Preparation of the free nonapeptide (59)

A solution of 0.020 g of the derivative (58) of step (e) in 5 ml of a mixture of CF$_3$COOH/anisol 10:1 (v/v), after 3 hours at ambient temperature while stirring is concentrated in the drier under vacuum. The residue is taken up in 40 ml of water. The aqueous solution is extracted with 20 ml of ethyl acetate and 20 ml of ether. The aqueous phase is lyophilised. The product obtained is homogeneous by thin-film chromatography in the mixtures of solvents G and H.

By rheophoresis under the conditions as previously described (for the peptides (16), (36), (37), (38), etc.), a single stain is obtained which migrates to $-3.15$ cm.

Analysis of amino acids after total acid hydrolysis: Asp 0.98; Ser 0.87; Glu 1.95; Gly 2.00; Ala 1.99.

EXAMPLE 11

Preparation of the Nonapeptide
Gln-Ala-Lys-Ser-Gln-Gly-Gly-Ser-Asn (32) and Derivatives of This Peptide The nonapeptide (32) is equivalent to the seric thymic hormone, with the sole difference of the N-terminal residue, Glutaminyl, which replaces the pyroglutamyl residue.

It is obtained by synthesis, using the following steps:

Step (a) Preparation of
Z-Ala-Lys(BOC)-Ser(But)-Gln-Gly-Gly-Ser(But)-Asn OBut (27)

This derivative is equivalent to the derivative (13), the synthesis of which is previously described (step h) of Example (1), the residue Gln not being masked by the 4,4-dimethoxy benzhydryl group (Mbh) and its preparation follows a different procedure from that employed for the synthesis of the derivative (13). To a solution of 0.080 g of Z-Ala-Lys(BOC)-Ser(But)-Gln-Gly-Gly-NHNH$_2$ (26) obtained in step (h) of Example 6, in 2 ml of DMF, cooled to $-40°$ C., are added 0.056 ml of an 8.3 N-solution of HCl/THF and then 0.016 ml of isoamyl nitrite. The solution is left for 20 minutes while stirring at $-40°$ C. and then there are added 0.13 ml of triethylamine and 0.0445 g of the acetate of Ser(But)-Asn OBut (2) (prepared in step d) 1° of Example 1). The solution is left while stirring for 2 hours at $-40°$ C. and for 48 hours at $-20°$ C. The solvent is evaporated under vacuum and the residue is triturated in water. The powder which is obtained is filtered and dried in the drier. The product (69 mg, yield 64%) is practically homogeneous by thin-film chromatography in the mixtures of solvents C and J.

M.p.=210° C., decomposition without fusion. This product is used directly for the following step.

Step (b) Preparation of the acetate of Ala-Lys(BOC)-Ser(But)-Gln-Gly-Gly-Ser(But)-Asn OBut (28)

A solution of 0.0322 g of the derivative (27) of the step (a) in solution in 4 ml of methanol, 0.1 ml of $CH_3COOH$ and 0.1 ml of water is subjected to a hydrogenation in the presence of 5% of Pd/C. After completing the reaction (controlled by TFC), filtering takes place and the filtrate is concentrated to dryness. The residue is dried in the drier over $P_2O_5$. Quantitative yield of a product which is practically homogeneous in the mixture of solvents J.

The product is used directly for the following steps.

Step (c) Preparation of BOC (Gln-Ala-Lys(BOC)-Ser(But)-Gln-Gly-Gly-Ser(But)-Asn OBut (31)

To a solution of 0.278 g of the derivative (28) of step (b) in 2 ml of DMF are added 0.016 g of BOC Gln-ONp (provided by SERVA) and 6 μl of triethylamine. The solution is left while stirring overnight at ambient temperature. The solvent is evaporated under vacuum and the residue is triturated in ether. 28 mg (yield 78%) of a product which has slight impurities by TFC are obtained. 13 mg of this product are recrystallised from methanol/water. A product homogeneous by TFC is obtained in the mixtures of solvents C and J.

M.p.=218° C. with decomposition.

Step (d) Preparation of the free nonapeptide (32)

2 mg of the purified derivative (31) are treated for 3 hours with 0.5 ml of trifluoroacetic acid. The acid is evaporated at ambient temperature in the drier and the residue is dried over $P_2O_5$ and KOH. The product obtained is redissolved in water and washed three times with ethyl acetate and then lyophilised. By thin-film chromatography in the mixtures of solvents H and G, there is found, in addition to the nonapeptide (32), a very small stain of equal Rf value as the nonapeptide PyroGlu-Ala-Lys-Ser-Gln-Gly-Gly-Ser-Asn (16) and (30).

By rheophoresis on Whatman 3 MM paper under a voltage of 600 volts for 45 minutes in the buffering substance consisting of water/pyridine/acetic acid: 1000/2.5/9, of pH 4.0, the glutaminyl nonapeptide (32) migrates to −0.5 cm and the impurity pyroglutamyl nonapeptide to +0.7 cm. In the 0.01 N formic acid buffer of pH 2.3, the Gln nonapeptide migrates to −4.9 cm and the impurity (PyroGlu nonapeptide) to −2.2 cm. Analysis in amino acids after total acid hydrolysis: Asp 1.12; Ser 1.99; Glu 2.00; Gly 2.10; Ala 1.06; Lys 0.82; $NH_3$ 3.45.

EXAMPLE 12

Preparation of PyroGlu-Ala-Lys-Ser-Gln-Gly-Gly-Ser-Asn (30) from the derivative (28) of step (b) of Example 11

To a solution of 0.0213 g of the derivative (28) in 2 ml of DMF are added 10 mg of PyroGlu OTcp (prepared according to J. C. Anderson et al., J. Chem. Soc., C, 1967, page 108) and 5 μl of triethylamine. The solution is left while stirring at ambient temperature for 24 hours. The forming precipitate is filtered, the DMF is evaporated under vacuum and the residue is triturated in ethyl acetate. 14.2 mg (yield 57%) of a product are obtained which, by TFC, presents a very small impurity negative to the ninhydrin, disclosed by the chlorine method in the mixtures of solvents A and C. 5 mg of this product are purified by preparative chromatography on a thin film (Merck silica plate with a thickness of 2 mm) in the mixture of solvents C. The product thus obtained is chromatographically pure in the solvents C and A and corresponds to the derivative PyroGlu-Lys(BOC)-Ser(But)-Gln-Gly-Gly-Ser(But)-Asn OBut (29).

From this purified product is obtained the free nonapeptide PyroGlu-Lys-Ser-Gln-Gly-Gly-Ser-Asn (30) by treatment with a 4 N solution of HCl/ethyl acetate. After evaporation of the solvents and drying over $P_2O_5$ and KOH, the residue is redissolved in water and, after the aqueous solution has been washed three times with ethyl acetate, the free peptide (30) is obtained by lyophilisation. The product is homogeneous by thin-film chromatography in the mixtures of solvents H and G.

Analysis of amino acids after total acid hydrolysis: Asp 1.00; Ser 1.72; Glu 1.89; Gly 1.94; Ala 0.96.

EXAMPLE 13

Preparation of the derivative Z-Gln-Ala-Lys-Ser-Gln-Gly-Gly-Ser-Asn (34)

This derivative is obtained from the derivative (28) obtained in step (b) of Example 11.

To a solution of 0.107 g of the derivative (28) in 5 ml of DMF, after cooling to 0°, are added 0.03 ml of NMM and then, after 5 minutes, 0.04 mg of Z-Gln OSu (prepared according to J. Beacham et al., J. Amer. Chem. Soc. 1971, 93, 5526) and the solution is left at ambient temperature. The reaction mixture solidifies. It is concentrated under vacuum and the residue is taken up by the minimum of hot methanol. After cooling to 0° C., the precipitate is filtered and it is rinsed with ether. The product obtained is homogeneous by thin-film chromatography in the mixtures of solvents C, E and I.

This product corresponds to the derivative Z-Gln-Ala-Lys(BOC)-Ser(But)-Gln-Gly-Gly-Ser(But)-Asn OBut (33).

Starting from this derivative and by elimination of the temporary protective groupings BOC and But by $CF_3COOH$/anisol 10/1 (v/v), under the same conditions as for the homologous derivative (18) of Example 2, there is obtained the nonapeptide derivative Z.Gln-Ala-Lys-Ser-Gln-Gly-Gly-Ser-Asn (34).

The product thus obtained is homogeneous by thin-film chromatography in the mixtures of solvents G and H. By rheophoresis under the conditions used for the other free nonapeptides, a single stain is obtained which migrates to −2.7 cm.

Analysis of aminoacids after total acid hydrolysis: Asp 1.02; Ser 1.89; Glu 1.92; Gly 2.00; Ala 0.94.

By catalytic hydrogenation of the nonapeptide derivative (34) under the conditions described for obtaining the nonapeptide (18) (step b) of Example (2), a product which is homogeneous by thin-film chromatography in the mixtures of solvents G and H and identical with the nonapeptide (18) obtained by synthesis by a different procedure is obtained.

The product thus obtained corresponds to the nonapeptide Gln-Ala-Lys-Ser-Gln-Gly-Gly-Ser-Asn (35).

Analysis of amino acids after total acid hydrolysis: Asp 1.01; Ser 1.83; Glu 1.85; Gly 2.00; Ala 0.97.

EXAMPLE 14

Preparation of the Nonapeptide analogues of Structure

PyroGlu-Ala-Lys-Ala-Gln-Gly-Gly-Ser-Asn (65)

PyroGlu-Ala-Lys-D-Ser-Gln-Gly-Gly-Ser-Asn (66)

PyroGlu-Ala-Lys-Thr Gly-Gly-Gly-Ser-Asn (67)

PyroGlu-Ala-Lys-(N-methyl-Ser)-Gln-Gly-Gly-Ser-Asn (64)

which correspond to the nonapeptide having the structure of the seric thymic hormone, with the only difference that the serine residue of the fourth position is replaced by the residues L-alanine, D-serine, L-threonine or N-methyl serine.

These analogues are obtained by synthesis, following the same steps as previously described for the synthesis of the nonapeptide PyroGlu-Ala-Lys-Ser-Gln-Gly-Gly-Ser-Asn (16) (cf. Example 1), with the sole difference that, at the step (c), and Z.Ser(But) is replaced by the derivatives Z.Ala, Z.D-Ser(But), Z.L-Thr(But) and Z-(N-methyl)-Ser.

In addition to the two synthesis procedures as previously described, the synthesis procedures which are numbered 3, 4, 5, 6, 7 and 8 have been used for obtaining a series of other derivatives of the STF, the steps thereof being hereinafter described.

The details are regards the preparation of the synthesis intermediaries according to these last procedures are quite similar to those of Examples 1 to 14.

Description of the Steps in the Synthesis of the STF Derivatives By the 3rd Procedure: (Peptides Nos. 61,62,63,82,83,84,87,91)

A—Preparation of the tetrapeptide derivative Z-Ser(But)-Gln-Gly-Gly-OH by saponification of the Z-Ser(But)-Gln-Gly-Gly-OMe derivative (21).

B—Synthesis of the hexapeptide derivative Z-Ser(But)-Gln-Gly-Ser(But)-Asn-OBut by coupling of the C-terminal dipeptide derivative (2) (Ser(But)-Asn-OBut acetate) with the mixed anhydride resulting from the isobutyl chlorocarbonate of the preceding tetrapeptide derivative and transformation of the hexapeptide derivative into its acetate by hydrogenolysis of the Z grouping.

C—Synthesis of the heptapeptide derivative Z-Lys-(Ac)-Ser(But)-Gln-Gly-Gly-Ser(But)-Asn-OBut by coupling the Z-Lys(Ac) derivative (prepared according to L. Benoiton, Can. J. Chem. 1963 (41), 1718) with the acetate of the preceding hexapeptide derivative, by the method using mixed anhydrides and transformation of the heptapeptide derivative into its acetate by hydrogenolysis of the Z grouping.

D—Preparation of the acetate of Ala-NHNHBOC by hydrogenolysis of the Z-Ala-NHNHBOC derivative (prepared according to N. Yanaihara, C. Yanaihara, T. Sakagami, T. Nakajima, T. Nakayama and K. Matsumoto, Chem. Pharm. Bull. Jap. 1973, 21, 616).

E—Synthesis of the PyroGlu-Ala-NHNHBOC derivative by coupling the preceding derivative with the PyroGlu-OTcp derivative (prepared according to J. C. Anderson; M. A. Barton, D. M. Hardy. G. W. Kenner, J. Preston and R. C. Scheppard, J. Chem. Soc. C., 1967, page 108).

F—Synthesis of the nonapeptide derivative: PyroGlu-Ala-Lys(Ac)-Ser(But)-Gln-Gly-Gly-Ser(But)-Asn-OBut by:

(a) preparation of the PyroGlu-Ala-NHNH₂ derivative by acidolysis of the BOC grouping of the derivative prepared under E;

(b) preparation of the PyroGlu-Ala-N₃ azide, starting from the preceding hydrazide, by the method of K. Medzihradszky et al (Acta Chim. Acad. Sci. Hung. 1962, 30, 105);

(c) coupling of this azide with the acetate of the heptapeptide derivative prepared under C.

G—Obtaining the free nonapeptide:

PyroGlu-Ala-Lys(Ac)-Ser-Gln-Gly-Gly-Ser-Asn (62)

by elimination of all the temporary protection groups in a single step as described in connection with step (f) of Example 10.

H—Obtaining the free heptapeptide:

Lys(Ac)-Ser-Gln-Gly-Gly-Ser-Asn (82)

starting with the acetate of the heptapeptide derivative prepared under C by elimination of all the temporary protective groups in a single step.

I—By replacing the derivative Z-Lys(Ac) by the derivatives Nps-D-Lys(BOC) and Nps.Orn(BOC) (prepared by the method of I. Barral and J. Savrda, Synthesis 1973, page 795) by the action of O-nitrophenyl sulphenyl thiocyanate on the copper complexes of the $N^6$-BOC-D-lysine [obtained according to R. Schwyzer and W. Rittel, Helv. Chim. Acta 1961, 20, 159] and the $N^5$-BOC-ornithine [obtained according to F. Marchiori, R. Rocchi, G. Vivaldi, A. Tamburro and E. Scoffone, J. Chem. Soc. C, 1967, page 81], respectively, and Z-Hep (synthesised by benzyloxycarbonylation of the L-heptylene prepared according to B. Sanborn and G. Hein, Biochemistry, 1968, 7, 3616), and by following the same synthesis method [the selective elimination of the Nps grouping is effected according to W. König (HoppeSeyler's Z. Physiol. Chem. 1971, 352, 2, and H. Klostermeyer and E. Schwertner (Z. Naturforschung 1973, 28b, 334)], the following heptapeptides are obtained:

D-Lys-Ser-Gln-Gly-Gly-Ser-Asn (83)

Orn-Ser-Gln-Gly-Gly-Ser-Asn (84)

Hep-Ser-Gln-Gly-Gly-Ser-Asn (87)

and also the nonapeptides:

PyroGlu-Ala-D-Lys-Ser-Gln-Gly-Gly-Ser-Asn (61)

PyroGlu-Ala-Orn-Ser-Gln-Gly-Gly-Ser-Asn (63)

PyroGlu-Ala-Hep-Ser-Gln-Gly-Gly-Ser-Asn (91)

Description of the Steps in the Synthesis of the Derivatives of by the 4th Procedure: (Peptides Nos. 65, 66, 67)

A—Synthesis of the tripeptide derivative Z-Gln-Gly-GlyOMe by coupling of the acetate of Gly-Gly-OMe (4) with the Z-Gln-ONp derivative (obtained according to Fluka).

B—Preparation of the Z-Gln-Gly-Gly-NHNH₂ derivative by hydrazinolysis of the preceding methyl ester.

C—Synthesis of the Z-Gln-Gly-Gly-Ser(But)-Asn-OBut pentapeptide derivative by coupling of the Z-Gln-Gly-Gly-N₃ azide (obtained from the preceding hydrazide according to R. H. Mazur and J. M. Schlatter, J. Org. Chem. 1964, 29, 3212) with the C-terminal dipeptide derivative (2) (acetate of Ser(But)-Asn-OBut). Transformation of the pentapeptide derivative into its acetate by hydrogenolysis of the Z grouping.

D—Synthesis of the hexapeptide derivative Z-Ala-Gln-Gly-Gly-Ser(But)-Asn-OBut by coupling the Z-Ala derivative (obtained according to Fluka) with the acetate of the preceding pentapeptide derivative by the method using mixed anhydrides. Transformation of the hexapeptide derivative into its acetate by hydrogenolysis of the Z grouping.

E—Synthesis of the tripeptide derivative PyroGlu-Ala-Lys(BOC)-NHNHZ by coupling the PyroGlu-Ala-N$_3$ azide (see 3rd procedure, step F (b)) with the Lys(BOC)-NHNHZ derivative (prepared according to C. Sakarellos, M. Sakarellos-Daitsiotis, D. Blanot, I. Barral, J. Savrda and E. Bricas, Bull. Soc. Chim. Fr., 1976, page 781).

F—Synthesis of the nonapeptide derivative PyroGlu-Ala-Lys(BOC)-Ala-Gln-Gly-Gly-Ser(But)-Asn-OBut by
(a) preparation of the PyroGlu-Ala-Lys(BOC)-NHNH$_2$ derivative by selective hydrogenolysis of the Z grouping;
(b) preparation of the PyroGlu-Ala-Lys(BOC)-N$_3$ azide, from the preceding hydrazide, by the method of R. H. Mazur and J. M. Schlatter (J. Org. Chem. 1964, 29, 3212);
(c) coupling of this azide with the acetate of the hexapeptide derivative prepared under D.

G—Obtaining the free nonapeptide:

PyroGlu-Ala-Lys-Gln-Ala-Gly-Gly-Ser-Asn (65)

by elimination of all the temporary protective groups in a single step, as described in step (f) of Example 10.

H—By replacing the Z-Ala derivative (step D) by the Z-Thr(But) derivatives (obtained according to Fluka) and Z-D-Ser-OPcp (prepared according to J. Kovacs, M. Q. Ceprini, C. A. Dupraz and G. N. Schmit, J. Org. Chem. 1967, 32, 3696), the nonapeptides are respectively obtained:
PyroGlu-Ala-Lys-Thr-Gln-Gly-Gly-Ser-Asn (67)

PyroGlu-Ala-Lys-D-Ser-Gln-Gly-Gly-Ser-Asn (66)

Description of the Steps in the Synthesis of the Derivatives of the TSF by by 5th Procedure: (Peptides Nos. 72, 88, 89, 92)

A—Synthesis of the Z-D-Ala-Gly-OMe dipeptide by coupling the Z-D-Ala (prepared according to M. Bergmann and L. Zervas, Ber. 1932, 65, 1192) with the glycine methylester (sold in the hydrochloride form by Messrs. Fluka). Transformation of the dipeptide into its acetate by hydrogenolysis of the Z grouping.

B—Synthesis of the Z-Gln(Mbh)-D-Ala-Gly-OMe tripeptide derivative by coupling the Z-Gln(Mbh) derivative (obtained according to W. König and R. Geiger, Chem. Ber. 1970, 103, 2041) with the acetate of the previously obtained dipeptide. Transformation of this tripeptide derivative into its acetate by hydrogenolysis of the Z grouping.

C—Synthesis of the Z-Ser(But)-Gln(Mbh)-D-Ala-Gly-OMe tetrapeptide derivative by coupling the Z-Ser(But) derivative (obtained according to Fluka) with the acetate by the previously obtained tripeptide derivative. Transformation of this tetrapeptide derivative into its acetate by hydrogenolysis of the Z grouping.

D—Synthesis of the pentapeptide derivative Z-Lys-(BOC)-Ser(But)-Gln(Mbh)-D-Ala-Gly-OMe by coupling the Z-Lys(BOC) derivative (obtained according to Fluka) with the acetate of the previously obtained tetrapeptide derivative.

E—Preparation of the pentapeptide derivative:
Z-Lys(BOC)-Ser(But)-Gln(Mbh)-D-Ala-Gly-OH by saponification of the methyl ester pentapeptide derivative as previously obtained.

F—Synthesis of the heptapeptide derivative:
Z-Lys(BOC)-Ser(But)-Gln(Mbh)-D-Ala-Gly-Ser(-But)-Asn-OBut by coupling the C-terminal dipeptide derivative (2) (acetate of Ser(But)-Asn-OBut) with the anhydride mixed with the isobutyl chlorocarbonate of the preceding pentapeptide derivative. Transformation of the heptapeptide derivative into its acetate by hydrogenolysis of the Z grouping.

G—Synthesis of the octapeptide derivative:
Z-Ala-Lys(BOC)-Ser(But)-Gln(Mbh)-D-Ala-Gly-Ser(But)-Asn-OBut by coupling the Z-Ala derivative (obtained according to Fluka) with the acetate of the previously obtained heptapeptide derivative Transformation of the octapeptide derivative into its acetate by hydrogenolysis of the Z grouping.

H—Synthesis of the nonapeptide derivative:
PyroGlu-Ala-Lys(BOC)-Ser(But)-Gln(Mbh)-D-Ala-Gly-Ser(But)-Asn-OBut by coupling the PyroGlu-OTcp derivative (prepared according to J. C. Anderson et al. J. Chem. Soc. C. 1967, page 108) with the acetate of the previously obtained octapeptide derivative.

I—Obtaining the free nonapeptide:

PyroGlu-Ala-Lys-Ser-Gln-D-Ala-Gly-Ser-Asn (89)

by elimination of all the temporary protective groups in a single step as described in connection with step (f) of Example 10.

J—Obtaining the free heptapeptide:

Lys-Ser-Gln-D-Ala-Gly-Ser-Asn (88)

from the acetate of the heptapeptide derivative prepared under F by elimination of all the temporary groups in a single step.

K—By replacing the Z-D-Ala derivative referred to in step A by the Z-Ala and Z-D-Leu derivatives, and by following the same synthesis procedure, the following nonapeptides are obtained
PyroGlu-Ala-Lys-Ser-Gln-Ala-Gly-Ser-Asn (72)

PyroGlu-Ala-Lys-Ser-Gln-D-Leu-Gly-Ser-Asn (92)

Description of the Steps in the Synthesis of the Derivatives of the STF by the 6th Procedure: (Peptides Nos. 86, 90, 93, 94, 95)

A—Synthesis of the protected C-terminal dipeptide Z-Ser(But)-D-Asn-OBut by coupling the Z-Ser(But) (obtained according to Fluka in the form of the DCHA salt) and the acetate of D-Asn-OBut (obtained by hydrogenolysis of the Z-D-Asn-OBut, which is itself obtained according to E. Schnabel and H. Schüssler, Liebigs Ann. Chem. 1965, 686, 229). Transformation of the protected dipeptide into its acetate by hydrogenolysis of the Z grouping.

B—Preparation of the acetate of the tetrapeptide derivative:

H-Ser(But)-Gln(Mbh)-Gly-Gly-OMe by hydrogenolysis of the Z grouping of the tetrapeptide derivative Z-Ser(But)-Gln(Mbh)-Gly-Gly-OMe (7).

C—Synthesis of the pentapeptide derivative:

Z-Lys(BOC)-Ser(But)-Gln(Mbh)-Gly-Gly-OMe by coupling the Z-Lys(BOC) (obtained according to Fluka) with the acetate of the previously obtained tetrapeptide derivative. Transformation of the pentapeptide derivative into its acetate by hydrogenolysis of the Z grouping.

D—Synthesis of the hexapeptide derivative:

Z-Ala-Lys(BOC)-Ser(But)-Gln(Mbh)-Gly-Gly-OMe by coupling the Z-Ala (obtained according to Fluka) with the acetate of the previously obtained pentapeptide derivative.

E—Preparation of the derivative:

Z-Ala-Lys(BOC)-Ser(But)-Gln(Mbh)-Gly-Gly-NHNH$_2$ by hydrazinolysis of the methyl ester of the preceding derivative.

F—Synthesis of the octapeptide derivative:

Z-Ala-Lys(BOC)-Ser(But)-Gln(Mbh)-Gly-Gly-Ser(But)-D-Asn-OBut by coupling the Z-Ala-Lys(BOC)-Ser(But)-Gln(Mbh)-Gly-Gly-N$_3$ azide which is obtained from the preceding hydrazide with the dipeptide acetate obtained under A. Transformation of the octapeptide derivative into its acetate by hydrogenolysis of the Z grouping.

G—Synthesis of the nonapeptide derivative:

PyroGlu-Ala-Lys(BOC)-Ser(But)-Gln(Mbh)-Gly-Gly-Ser(But)-D-Asn-OBut by coupling the PyroGlu-OTcp derivative (prepared according to J. C. Anderson et al, J. Chem. Soc. C. 1967, page 108) and the acetate of the preceding octapeptide derivative.

H—Obtaining the free nonapeptide:

PyroGlu-Ala-Lys-Ser-Gln-Gly-Gly-Ser-D-Asn (90)

by elimination of all the temporary protective groups in a single step as described in step (f) of Example 10.

I—By replacing the D-Asn-OBut acetate in step A by the β-Ala-NH$_2$ acetate (obtained according to H. T. Hanson and E. L. Smith, J. Biol. Chem. 1948, 175, 833) and the H-Asn-NH$_2$ hydrobromide (obtained according to M. Bodanszky, Y. S. Klausmer and V. Mutt, Bioorg. Chem. 1972, 2, 30), the following nonapeptides are respectively obtained, by using the same synthesis procedure:

PyroGlu-Ala-Lys-Ser-Gln-Gly-Gly-Ser-β-Ala-NH$_2$ (86)

PyroGlu-Ala-Lys-Ser-Gln-Gly-Gly-Ser-Asn-NH$_2$ (93)

J—Synthesis of the C-terminal dipeptides:

Z-Thr(But)-Asn-OBut

Z-D-Ser-Asn-OBut by coupling the Asn-Obut derivative (obtained according to E. Schnabel and H. Schüssler, Liebigs Ann. Chem. 1965, 686, 229) respectively with the Z-Thr(But) derivatives (obtained according to Fluka) and the Z-D-Ser-OPcp derivatives (prepared according to J. Kovacs et al, J. Org. Chem. 1967, 32, 3696). Starting with these two dipeptide derivatives, and using the same synthesis procedure, the following nonapeptides are obtained:

PyroGlu-Ala-Lys-Ser-Gln-Gly-Gly-Thr-Asn (94)

PyroGlu-Ala-Lys-Ser-Gln-Gly-Gly-D-Ser-Asn (95)

Description of the Steps in the Synthesis of the STF Derivatives by the 7th Procedure: (Peptides Nos. 68, 71, 96, 97, 98, 99)

A—Synthesis of the tetrapeptide derivative Z-Gly-Gly-Ser(But)-Asn-OBut by coupling the C-terminal dipeptide derivative (2) (Ser(But)-Asn-OBut acetate) with the Z-Gly-Gly derivative (prepared by benzyloxycarbonylation of the glycyl glycine obtained according to Sigma). Transformation of the tetrapeptide derivative into its acetate by hydrogenolysis of the Z grouping.

B—Synthesis of the pentapeptide derivative:

Z-Glu-(OBut)-Gly-Gly-Ser(But)-Asn-OBut by coupling the Z-Glu(OBut) derivative (obtained according to Fluka) with the acetate of the preceding tetrapeptide derivative. Transformation of the pentapeptide derivative into its acetate by hydrogenolysis of the Z grouping.

C—Synthesis of the hexapeptide derivative:

Z-Ser(But)-Glu(OBut)-Gly-Gly-Ser(But)-Asn-OBut by coupling the Z-Ser(But) derivative (obtained according to Fluka) with the acetate of the preceding pentapeptide derivative. Transformation of the hexapeptide derivative into its acetate by hydrogenolysis of the Z grouping.

D—Synthesis of the heptapeptide derivative:

Nps-Lys(BOC)-Ser(But)-Glu(OBut)-Gly-Gly-Ser(But)-Asn-OBut by coupling the Nps-Lys(BOC) derivative (obtained according to J. Barrall and J. Savrda, Synthesis 1973, page 795) with the preceding hexapeptide derivative. Transformation of the heptapeptide derivative into its hydrobromide by selective elimination of the Nps grouping in accordance with W. König (Hoppe-Seyler's Z. Physiol. Chem. 1971, 352, 2) and H. Klostermeyer and E. Schwertner (Z. Naturforschung 1973, 28b, 334).

E—Synthesis of the nonapeptide derivative:

PyroGlu-Ala-Lys(BOC)-Ser(but)-Glu(OBut)-Gly-Gly-Ser(But)-Asn-OBut by coupling the PyroGlu-Ala-N$_3$ azide (see the 3rd procedure, step F (b)) with the hydrobromide of the preceding heptapeptide derivative.

F—obtaining the free nonapeptide:

PyroGlu-Ala-Lys-Ser-Glu-Gly-Gly-Ser-Asn (68)

by elimination of all the temporary protective groups in a single step, as described in step (f) of Example 10.

G—By replacing the Z-Glu(OBut) derivative in step B by the Z-D-Gln(Mbh), Z-Asn(Mbh), Z-Nva, Nps-Cys(S-CONH$_2$) and Nps-Met(O) derivatives, the following nonapeptides are respectively obtained:

PyroGlu-Ala-Lys-Ser-D-Glu-Gly-Gly-Ser-Asn (71)

PyroGlu-Ala-Lys-Ser-Asn-Gly-Gly-Ser-Asn (96)

PyroGlu-Ala-Lys-Ser-Nva-Gly-Gly-Ser-Asn (97)

PyroGlu-Ala-Lys-Ser-Cys(S-CO-NH$_2$)-Gly-Gly-Ser-Asn (98)

PyroGlu-Ala-Lys-Ser-Met(O)-Gly-Gly-Ser-Asn (99)

Description of the steps in the Synthesis of the STF Derivatives by the 8th Procedure: (Peptides Nos. 73, 100, 101, 102, 103, 104)

A—Synthesis of the tripeptide derivative Z-D-Ala-Ser(But)-Asn-OBut by coupling the Z-D-Ala (prepared according to M. Bergmann and L. Zervas, Ber. 1932, 65, 1192) with the C-terminal dipeptide derivative (2) (Ser(But)-Asn-OBut acetate). Transformation of the tripeptide derivative into its acetate by hydrogenolysis of the Z grouping.

B—Synthesis of the dipeptide derivative Z-Gln(Mbh)-Gly-OMe by coupling the Z-Gln(Mbh) (obtained according to W. König and R. Geiger, Chem. Ber. 1970, 103, 2041) with the glycine methylester (sold in hydrochloride form by Messrs. Fluka). Transformation of the dipeptide derivative into its acetate by hydrogenolysis of the Z grouping.

C—Synthesis of the tripeptide derivative Z-Ser(But)-Gln(Mbh)-Gly-OMe by coupling of the Z-Ser(But) (obtained according to Fluka) with the acetate of the preceding dipeptide derivative. Transformation of the tripeptide derivative into its acetate by hydrogenolysis of the Z grouping.

D—Synthesis of the tetrapeptide derivative Z-Lys(-BOC)-Ser(But)-Gln (Mbh)-Gly-OMe by coupling the Z-Lys(BOC) (obtained according to Fluka) with the acetate of the preceding tripeptide derivative. Transformation of the tetrapeptide derivative into its acetate by hydrogenolysis of the Z grouping.

E—Synthesis of the pentapeptide derivative:
Z-Ala-Lys(BOC)-Ser(But)-Gln(Mbh)-Gly-OMe by coupling the Z-Ala (sold by Fluka) with the acetate of the preceding tetrapeptide derivative.

F—Preparation of the pentapeptide derivative:
Z-Ala-Lys(BOC)-Ser(But)-Gln(Mbh)-Gly-OH by saponification of the methyl ester of the preceding pentapeptide derivative.

G—Synthesis of the octapeptide derivative:
Z-Ala-Lys(BOC)-Ser(But)-Gln(Mbh)-Gly-D-Ala-Ser(But-Asn.OBut by coupling the acetate of the tripeptide derivative prepared under A with the anhydride mixed with the isobutyl chlorocarbonate of the preceding pentapeptide derivative. Transformation of the octapeptide derivative into its acetate by hydrogenolysis of the Z grouping.

H—Synthesis of the nonapeptide derivative:
PyroGlu-Ala-Lys(BOC)-Ser(But)-Gln(Mbh)-Gly-D-Ala-Ser(But)-Asn-OBut by coupling the PyroGlu-OTcp derivative (prepared according to J. C. Anderson et al, J. Chem. Soc. C. 1967, page 108) with the acetate of the previously obtained octapeptide derivative.

I—Obtaining the free nonapeptide:

PyroGln-Ala-Lys-Ser-Gln-Gly-D-Ala-Ser-Asn (100)

by elimination of all the temporary protective groups in a single step, as described in step (f) of Example 10.

J—By replacing the Z-D-Ala derivative in step A by the Z-Ala-, Z-Sar, Z-D-Leu and Z-Gly-Gly derivatives, there are respectively obtained the nonapeptides:

PyroGlu-Ala-Lys-Ser-Gln-Gly-Ala-Ser-Asn (73)

PyroGlu-Ala-Lys-Ser-Gln-Gly-Sar-Ser-Asn (101)

PyroGlu-Ala-Lys-Ser-Gln-Gly-D-Leu-Ser-Asn (102)

and the decapeptide:
PyroGlu-Ala-Lys-Ser-Gln-Gly-Gly-Gly-Ser-Asn (103)

K—By replacing the tripeptide derivative in step G by the dipeptide derivative (2) (Ser(But)-Asn-OBut acetate), there is obtained the octapeptide:

PyroGlu-Ala-Lys-Ser-Gln-Gly-Ser-Asn (104)

Other derivatives of the STF, prepared by the 1st procedure: (Peptides Nos. 85, 105, 106, 107, 108, 109, 110)

A—By selective acidolysis of the BOC and But groupings of the derivative

Z-Lys-(BOC)-Ser(But)-Gln(Mbh)-Gly-Gly-Ser(But)-Asn-OBut (11)

and the derivative Z-Ala-Lys(BOC)-Ser(But)-Gln(Mbh)-Gly-Gly-Ser(But)-Asn-OBut (13), there is obtained the heptapeptide Z-Lys-Ser-Gln-Gly-Gly-Ser-Asn (85)

and the octapeptide:

Z-Ala-Lys-Ser-Gln-Gly-Gly-Ser-Asn (105)

B—As a result of the replacement, in step ($I_1$) of the procedure 1, of the PyroGlu-OTcp derivative by the derivatives D-PyroGlu-OTcp, Z-D-Gln(Mbh), Nps-Cys(S-CONH$_2$), BOC-Pro and L-Aad-OTcp, there are respectively obtained the nonapeptides:
D-PyroGlu-Ala-Lys-Ser-Gln-Gly-Gly-Ser-Asn (106)

D-Gln-Ala-Lys-Ser-Gln-Gly-Gly-Ser-Asn (107)

Cys(S-CONH$_2$)-Ala-Lys-Ser-Gln-Gly-Gly-Ser-Asn (108)

Pro-Ala-Lys-Ser-Gln-Gly-Gly-Ser-Asn (109)

<Aad-Ala-Lys-Ser-Gln-Gly-Gly-Ser-Asn (110)

Another STF Derivative Prepared by the 2nd Procedure: (Peptide No. 79)

A—Synthesis of the dipeptide derivative:
Z-Ser(But)-Gln-OBut by coupling the Z-Ser(But) derivative (obtained according to Fluka) and the Gln-OBut derivative (prepared according to E. Schnabel and H. Schüssler, Leibigs Ann. Chem. 1965, 686, 229). Transformation of the dipeptide derivative into its acetate by hydrogenolysis of the Z grouping.

B—By following the 2nd synthesis procedure, and by using the preceding derivative, there is obtained the nonapeptide:

PyroGlu-Ala-Lys-Ser-Gln-Gly-Gly-Ser-Gln (79)

Preparation of the Derivatives of the STF by Guanidination of the Synthetic Compounds: (Peptides Nos. 111 and 112)

By guanidination at pH 10.5° and 4° C., by means of the O-methyl (isourea) (marketed in sulphate form by Messrs. Serva), of the peptide (63) and of the synthetic STF (16), followed by purification by preparative electrophoresis under high voltage, there are respectively obtained the peptides:

PyroGlu-Ala-Arg-Ser-Gln-Gly-Gly-Ser-Asn (111)

PyroGlu-Ala-Har-Ser-Gln-Gly-Gly-Ser-Asn (112)

Preparation of the Derivatives of the STF by Acetylation of Synthetic Compounds: (Peptides Nos. 113, 114, 115, 116)

A—By acetylation (according to M. Reboud-Ravaux and C. Chelis (Eur. J. Biochem 1976, 65, 25), by means of acetyl benzotriazole, of the nonapeptides (89), (61) and (90), there are respectively obtained the following $N^6$-acetylated nonapeptides:

PyroGlu-Ala-Lys(Ac)-Ser-Gln-D-Ala-Gly-Ser-Asn (113)

PyroGlu-Ala-D-Lys(Ac)-Ser-Gln-Gly-Gly-Ser-Asn (114)

PyroGlu-Ala-Lys(Ac)-Ser-Gln-Gly-Gly-Ser-D-Asn (115)

B—This method, applied to the derivative (14) (acetate of Z-Ala-Lys(BOC)-Ser(But)-Gln(Mbh)-Gly-Gly-Ser(But)-AsnOBut) and followed by a selective acidolysis of the BOC and But groupings, yields the following $N\alpha$-acetylated octapeptide Ac-Ala-Lys-Ser-Gln-Gly-Gly-Ser-Asn (116)

Pharmacological Properties and Therapeutic Applications

As previously indicated, the polypeptides of the invention either have a thymic activity equal to or better than that of the natural thymic hormone, or show an antagonistic or inhibiting action with respect to the thymic hormone.

Tests in vivo and in vitro have been carried out on the polypeptides of the invention.

For the tests in vitro, use has been made of the rosette test as hereinafter described:

Determination of the Thymic Activity of the Polypeptides by the Rosette Test

The rosette test has been previously described by J. F. Bach and M. Dardenne in Immunology, 25, 353 (1973), the contents of this article being incorporated herein by reference.

The thymic activity of the polypeptide is established by incubation in a hemolysis tube with $3 \times 10^6$ cells of the spleen originating from adult C 57/B1 6 mice (supplied by the Centre d'Elevage des Animaux de Laboratoire of C.N.R.S. (45 Orleans, La Source), thymectomised 10 to 20 days previously. The thymectomy method is described by M. Dardenne and J. F. Bach in Immunology, 25, 343 (1973) on page 344. The contents of this article are incorporated herein by reference.

The incubation is carried out for 90 minutes at 37° C. in the presence of azathioprine (Az) at a concentration of 10 µg/ml.

This concentration is intermediate between the minimal concentration of Az inhibiting 50% of the cells of the spleen forming rosettes (RFC) coming from normal mice (1 µg/ml) and coming from thymectomised adult mice (25–10 µg/ml). On completion of the incubation, $12 \times 10^6$ red cells from sheep's blood (SRBC) are added to the cells in the test specimen. The cells in the specimen are centrifuged for 6 minutes at 200 g and carefully brought gently into suspension by rotation on a roller (diameter 10 cm) at a low speed (10 r.p.m.). The RFC are counted in a hematocytometer. In the absence of thymic activity, the number of RFC is $1210/10^6$ cells ± 120 (standard deviation SD). In the presence of thymic activity, the quantity of RFC is reduced to a level of 200 to $400/10^6$ cells. In the absence of Az, the peptides do not cause inhibition of the RFC. The thymic activity is defined as the inhibition of more than 50% of the rosette-forming cells.

The peptides were tested in vitro in the rosette test as described above, where certain of them were found to be active at concentrations below 1 pg/ml. This effect is specific, since control peptides of similar molecular weight, such as angiotensine and the substance P, are inactive.

The peptides active in vitro were also checked in tests carried out in vivo. Injected into 6 weeks old thymectomised mice and used 8 weeks after the thymectomy, the peptides produce the appearance at the 15th minute in the serum of a biological activity conferring the sensitivity to the azothioprine of the spleen cells forming rosettes. This activity, which is also observed with the initial peptide, is again found for peptide dilutions greater than 1/1000.

Concurrently, the spleen cells of mice treated with the peptides see the correction of the sensitivity of the cells forming rosettes with respect to the azathioprine and the anti-theta serum, this indicating that these cells have acquired the expression of cell markers T, which they did not previously have. These experiments were repeated with different doses of peptide: 10 and 100 pg, 1 and 10 ng, this making possible the demonstration of a dose-effect relationship and the showing of the absence of acute toxicity, whether the product is injected by itself (in physiological serum) or adsorbed on carboxymethyl cellulose.

The results of the tests which are obtained for certain compounds of the invention are set out in the following Tables I to IV.

The tests being used are as follows:

(1) Activity in vitro in the rosette test.

(2) Activity in vivo (study of the serum 2 hours and 4 hours after injection into thymectomised mice in different quantities (0.1, 1 or 10 ng) of peptide absorbed on carboxymethyl cellulose).

(3) Correction of the abnormal reactivity of the cells forming the rosettes of the spleen with azathioprine in thymectomised mice 24 hours after injecting the peptide (0.1, 1 and 10 ng) bonded to the carboxymethyl cellulose.

(4) Kinetics of the activity in the serum after injection of 0.1 or 1 ng of peptide without carboxymethyl cellulose with a view to finding the active peptides which have a retarding activity.

(5) Investigation in vitro of the inhibiting or antagonising activity of the inactive polypeptides.

TABLE I

| No | Peptide | Activity in vitro | Activity in vivo | Bonding with the antibodies |
|---|---|---|---|---|
| 38 | Ala—Lys—Ser—Gln—Gly—Gly—Ser—Asn | + | + | + |
| 42 | PyroGlu—Ala—Lys—Ser—Gln—Gly—Gly—Ser | − | − | − |
| 53 | PyroGlu—Ala—Lys—Ser—Gln—Gly—Gly—Ser—Asp | − | − | − |
| 59 | PyroGlu—Ala—Lys—Ser—Gln—Gly—Gly—Ala—Asn | − | − | + |
| 18 | Gln—Ala—Lys—Ser—Gln—Gly—Gly—Ser—Asn | + | + | + |
| 34 | Z—Gln—Ala—Lys—Ser—Gln—Gly—Gly—Ser—Asn | + | + | + |
| 37 | Lys—Ser—Gln—Gly—Gly—Ser—Asn | + | + | + |
| 47 | PyroGlu—D-Ala—Lys—Ser—Gln—Gly—Gly—Ser—Asn | − | − | + |
| 45 | D-Ala—Lys—Ser—Gln—Gly—Gly—Ser—Asn | − | − | + |
| 36 | Ser—Gln—Gly—Gly—Ser—Asn | − | − | − |
| 79 | PyroGlu—Ala—Lys—Ser—Gln—Gly—Gly—Ser—Gln | − | − | − |
| 66 | PyroGlu—Ala—Lys—D-Ser—Gln—Gly—Gly—Ser—Asn | − | − | − |
| 65 | PyroGlu—Ala—Lys—Ala—Gln—Gly—Gly—Ser—Asn | − | − | − |
| 82 | Lys($N^6$—acetyl)—Ser—Gln—Gly—Gly—Ser—Asn | − | − | + |
| 83 | D-Lys—Ser—Gln—Gly—Gly—Ser—Asn | − | − | + |
| 84 | Orn—Ser—Gln—Gly—Gly—Ser—Asn | − | − | + |
| 85 | $N^\alpha$Z—Lys—Ser—Gln—Gly—Gly—Ser—Asn | − | − | + |
| 62 | PyroGlu—Ala—Lys($N^6$—acetyl)—Ser—Gln—Gly—Gly—Ser—Asn | − | +R | + |
| 61 | PyroGlu—Ala—D-Lys—Ser—Gln—Gly—Gly—Ser—Asn | + | +R | + |
| 63 | PyroGlu—Ala—Orn—Ser—Orn—Gly—Gly—Ser—Asn | − | − | + |
| 86 | PyroGlu—Ala—Lys—Ser—Gln—Gly—Gly—Ser—$\beta$Ala—$NH_2$ | + | + | − |
| 87 | Hep—Ser—Gln—Gly—Gly—Ser—Asn | − | − | + |
| 88 | Lys—Ser—Gln—D-Ala—Gly—Ser—Asn | − | − | + |
| 89 | PyroGlu—Ala—Lys—Ser—Gln—D-Ala—Gly—Ser—Asn | − | +R | + |
| 90 | PyroGlu—Ala—Lys—Ser—Gln—Gly—Gly—Ser—D-Asn | − | +R | + |

In the above Table I, the peptides according to the invention are identified by their respective numbers as used in this specification.

As regards the activity, the + and − symbols respectively indicate that the peptide is active or inactive. The symbol R indicates that the peptide has a retarding activity.

The suitability of the peptides for being bonded to the antibodies is indicated by the + and − symbols, which respectively signify that the peptide is bonded or is not bonded to the antibodies.

The results of the above Table I are set out in detail in the following Tables II, III and IV.

TABLE II

| No | Active concentration (ng/ml) (test in vitro) | Serums (test in vivo) 2 hours after injection | | Spleens (test in vivo) 24 hours after injection | | Bonding with the antibodies |
|---|---|---|---|---|---|---|
| | | Quantity injected (ng) | Active Dilutions | Quantity injected (ng) | Quantity of azathioprine (µg) | |
| 38 | $2.10^{-6}$ | | | | | |
| | $7.10^{-6}$ | 1 | $\frac{1}{64000}$ $\frac{1}{256000}$ $\frac{1}{256000}$ | 1 | 0,3 0,3 0,3 | + |
| | $2.10^{-6}$ | 10 | $\frac{1}{128000}$ $\frac{1}{512000}$ $\frac{1}{512000}$ | 10 | 0,3 0,3 | |
| 42 | <0,03 | 1 | $\frac{1}{1000}$ $\frac{1}{1000}$ $<\frac{1}{1000}$ | 1 | 25 50 50 | − |
| | <0,03 | 10 | $<\frac{1}{1000}$ $<\frac{1}{1000}$ $\frac{1}{2000}$ | 1 | 6 25 6 | |
| 53 | <0,03 | 0,1 | $<\frac{1}{1000}$ $\frac{1}{1000}$ $\frac{1}{1000}$ | 0,1 | 50 25 50 | − |
| | <0,03 | 1 | $<\frac{1}{1000}$ $\frac{1}{2000}$ $\frac{1}{2000}$ | 1 | 25 50 50 | |
| 59 | 0,03 | 0,1 | $\frac{1}{4000}$ $\frac{1}{8000}$ $\frac{1}{8000}$ | 0,1 | 50 25 50 | + |
| | <0,03 | 1 | $<\frac{1}{1000}$ $\frac{1}{4000}$ $\frac{1}{8000}$ | 1 | 50 25 50 | |
| 18 | $7.10^{-6}$ | 0,1 | $\frac{1}{128000}$ $\frac{1}{256000}$ $\frac{1}{512000}$ | 0,1 | 0,3 0,7 0,3 | + |
| | $7.10^{-6}$ | | $\frac{1}{512000}$ $\frac{1}{512000}$ $\frac{1}{512000}$ | | 0,3 0,3 0,3 | |
| | $3.10^{-6}$ | | | | | |
| 34 | $2.10^{-6}$ | 0,1 | $\frac{1}{128000}$ $\frac{1}{256000}$ $\frac{1}{256000}$ | 0,1 | 0,3 0,3 0,7 | + |
| | $2.10^{-6}$ | 1 | $\frac{1}{256000}$ $\frac{1}{256000}$ $\frac{1}{256000}$ | 1 | 0,3 0,7 0,3 | |
| 37 | 0,03 | 0,1 | $\frac{1}{64000}$ $\frac{1}{32000}$ $\frac{1}{32000}$ | 0,1 | 25 25 25 | + |
| | 0,007 | 10 | $\frac{1}{256000}$ $\frac{1}{128000}$ $\frac{1}{128000}$ | 10 | 6 12 3 6 | |

TABLE II-continued

| No | Active concentration (ng/ml) (test in vitro) | Serums (test in vivo) 2 hours after injection | | | Spleens (test in vivo) 24 hours after injection | | Bonding with the antibodies |
|---|---|---|---|---|---|---|---|
| | | Quantity injected (ng) | Active Dilutions | | Quantity injected (ng) | Quantity of azathioprine (μg) | |
| 47 | <0,03 | 1 | $<\frac{1}{125}$ $<\frac{1}{250}$ $\frac{1}{500}$ | | 1 | 50 50 50 | + |
| | <0,03 | 10 | $\frac{1}{125}$ $\frac{1}{125}$ $\frac{1}{125}$ | | 10 | 25 50 25 | |
| 45 | <0,03 | 0,1 | $\frac{1}{500}$ $\frac{1}{500}$ $\frac{1}{500}$ $\frac{1}{1000}$ $\frac{1}{1000}$ $\frac{1}{1000}$ | | 0,1 | 25 25 25 50 50 50 12 | + |
| 36 | 0,3 | 1 | $<\frac{1}{125}$ $<\frac{1}{125}$ $<\frac{1}{125}$ | | 1 | 50 50 50 | — |
| | 0,6 | | | | | | |
| 79 | <0,03 | 0,1 | $<\frac{1}{250}$ $<\frac{1}{250}$ $<\frac{1}{250}$ | | 0,1 | 25 25 50 | — |
| 66 | <0,03 | 0,1 | $<\frac{1}{250}$ $<\frac{1}{250}$ $<\frac{1}{250}$ | | 0,1 | 50 50 50 | + |
| 65 | <0,03 | 0,1 | $<\frac{1}{250}$ $<\frac{1}{250}$ $<\frac{1}{250}$ | | 0,1 | 50 50 50 | + |
| 82 | <0,03 | 0,1 | $<\frac{1}{250}$ $<\frac{1}{250}$ $<\frac{1}{250}$ | | 0,1 | 50 50 50 | + |
| 83 | <0,03 | 0,1 | $\frac{1}{250}$ $\frac{1}{250}$ $\frac{1}{250}$ | | 0,1 | 50 50 50 | + |
| 84 | <0,03 | 0,1 | $\frac{1}{250}$ $<\frac{1}{250}$ $<\frac{1}{250}$ | | 0,1 | 50 50 50 | + |
| 85 | $1.10^{-3}$ | 0,1 | $<\frac{1}{250}$ $<\frac{1}{250}$ $<\frac{1}{250}$ | | 0,1 | 50 50 25 | + |

TABLE III

| No | Active concentration (ng/ml) (test in vitro) | Serums (test in vivo) 2 hours after injection | | Serums (test in vivo) 4 hours after injection | |
|---|---|---|---|---|---|
| | | Quantity injected (ng) | Active Dilutions | Quantity injected (ng) | Active Dilutions |
| 62 | <0,06 | 0,1 | $\frac{1}{2000}$ $\frac{1}{4000}$ $\frac{1}{4000}$ $\frac{1}{8000}$ $\frac{1}{4000}$ | 0,1 | $\frac{1}{128000}$ $\frac{1}{128000}$ $\frac{1}{256000}$ |
| 61 | $2.10^{-6}$ | 0,1 | $\frac{1}{256000}$ $\frac{1}{512000}$ $\frac{1}{512000}$ | 0,1 | $\frac{1}{256000}$ $\frac{1}{512000}$ $\frac{1}{512000}$ |
| 63 | <0,03 | 0,1 | $\frac{1}{1000}$ $\frac{1}{1000}$ $<\frac{1}{1000}$ | 0,1 | $<\frac{1}{1000}$ $\frac{1}{1000}$ $\frac{1}{1000}$ |
| 86 | $7.10^{-3}$ | 0,1 | $\frac{1}{64000}$ $\frac{1}{64000}$ $\frac{1}{64000}$ | 0,1 | $\frac{1}{32000}$ $\frac{1}{32000}$ $\frac{1}{32000}$ |
| 87 | <0,03 | 0,1 | $\frac{1}{4000}$ $\frac{1}{4000}$ $\frac{1}{4000}$ | 0,1 | $\frac{1}{8000}$ $\frac{1}{8000}$ $\frac{1}{8000}$ |
| 88 | | 0,1 | $\frac{1}{500}$ $\frac{1}{1000}$ $\frac{1}{1000}$ $\frac{1}{1000}$ | 0,1 | $\frac{1}{1000}$ $\frac{1}{2000}$ $\frac{1}{1000}$ $\frac{1}{1000}$ |
| 89 | <0,03 | 0,1 | $\frac{1}{500}$ $\frac{1}{1000}$ $\frac{1}{1000}$ $\frac{1}{500}$ | 0,1 | $\frac{1}{32000}$ $\frac{1}{128000}$ $\frac{1}{128000}$ |
| 90 | <0,03 | 0,1 | $\frac{1}{128000}$ $\frac{1}{128000}$ | 0,1 | $\frac{1}{64000}$ $\frac{1}{64000}$ |
| | <0,03 | | $\frac{1}{128000}$ $\frac{1}{128000}$ | | $\frac{1}{128000}$ $\frac{1}{128000}$ |

TABLE IV

| No | Spleens (test in vivo) 24 hours after injection | | Spleens (test in vivo) 48 hours after injection | | Bonding with the antibodies |
|---|---|---|---|---|---|
| | Quantity injected (ng) | Quantity of azathioprine (μg) | Quantity injected (ng) | Quantity of azathioprine (μg) | |
| 62 | 0,1 | 6 6 3 1,5 3 6 | 1 | 12 12 12 3 12 6 | |
| | | | 10 | 3 3 1,5 | + |
| | | | 50 | 0,7 0,7 0,7 1,5 1,5 | |
| 61 | 0,1 | 0,7 0,7 1,5 | 1 | 50 50 50 | |
| | | | 10 | 25 25 50 | + |
| | | | 50 | 6 12 12 | |
| 63 | 0,1 | 50 50 50 | | | + |
| 86 | 0,1 | 12 | | | — |
| 87 | 0,1 | 3 3 | | | + |
| 88 | 0,1 | 50 50 25 25 | | | + |
| 89 | 0,1 | 6 6 12 | 1 | 25 25 25 | |

TABLE IV-continued

| | Spleens (test in vivo) 24 hours after injection | | | Spleens (test in vivo) 48 hours after injection | | | | |
|---|---|---|---|---|---|---|---|---|
| No | Quantity injected (ng) | Quantity of azathioprine (μg) | | Quantity injected (ng) | Quantity of azathioprine (μg) | | | Bonding with the antibodies |
| | | | | 10 | 12 | 6 | 6 | + |
| | | | | 50 | 3 | 3 | 1,5 | |
| 90 | 0,1 | 6 | 12 | 12 | | | | + |

Set out in Tables II and III are the results of the rosette test (test in vitro), by expressing, for each of the tested peptides, the concentration of active peptide (in ng/ml) in this test. This active concentration in the rosette test has been established by the procedure which has been previously described.

The results of the tests in vivo on the serum and on the spleen, set out in Tables II, III and IV, were established by the procedure as previously indicated. The tests on the serum were carried out by injecting, into thymectomised mice, a determined quantity of polypeptide (0.1, 1 or 10 ng) absorbed on carboxymethyl cellulose, by sampling their serum after a set time (2 hours after the injection and possibly also 4 hours after injection) and by determining the dilutions of serum showing a biological activity which compares or checks the sensitivity to azathioprine of the spleen cells forming rosettes.

The tests on the spleen were carried out by determining the quantity of azathioprine which is necessary for inhibiting the rosette-forming cells of the spleen of thymectomised mice after an established time (24 hours and possibly also 48 hours) after the injection of an established quantity of polypeptide (0.1, 1 or 10 ng).

After studying the results given in the foregoing Tables, the result is that the active polypeptides are the compounds 38, 18, 34, 37, 62, 61, 86, 89 and 90.

The inactive polypeptides are the compounds 42, 53, 59, 47, 45, 36, 79, 66, 65, 82, 83, 84, 85, 63, 87 and 88.

Among the active polypeptides, certain of them still show an appreciable activity 4 hours after injection in the test in vivo on the serum (cf. Table III) and 48 hours after injection in the test in vivo on the spleen (cf. Table IV). These polypeptides which show this retarding activity are the polypeptides 62, 61, 89 and 90.

These polypeptides were subjected to the test No. 4 as indicated above in order to follow the kinetics of the activity in the serum after injection of 0.1 or 1 ng of peptide without carboxymethyl cellulose to thymectomised mice, following the active dilutions of serum as a function of the time after the injection.

These kinetics have also been established for active products, but without any delay action, by way of comparison.

The results of these tests have been established in the form of curves in FIGS. 1, 2 and 3 of the accompanying drawings.

Represented in FIG. 1 are the curves which express the variations in active serum dilutions as a function of time after injection of 1 ng of polypeptide (not bonded with the carboxymethyl cellulose) into thymectomised mice. The established curves correspond to 4 active polypeptides, but without delay-action, namely, the STF and polypeptides 34, 37 and 45.

It is established that these 4 polypeptides show a peak in activity at about 15 minutes after injection and that this activity then decreases very rapidly in time.

FIG. 2 shows 4 curves established under similar conditions for the STF by itself, STF bonded to carboxymethyl cellulose and the polypeptides 61 and 62 which are not bonded to the carboxymethyl cellulose.

The STF by itself shows a peak in activity at about 15 minutes and the activity then decreases very quickly. The STF bonded with carboxymethyl cellulose shows an activity peak at about 90 minutes, the carboxymethyl cellulose permitting the activity of the STF to be retarded.

The polypeptides 61 and 62 respectively show an activity peak at about 30 minutes and 45 minutes.

FIG. 3 shows 3 curves which have been established under similar conditions in respect of the STF bonded to the carboxymethyl cellulose and the polypeptides 89 and 90.

The polypeptides 89 and 90 show an activity peak in the region of 60 minutes and as a consequence represent delay-action products which are of particular interest.

The inactive polypeptides were subjected to the test No. 5 as previously indicated.

This test in vitro for investigating the inhibiting or antagonising activity of the inactive analogous peptides consists in incubating the inactive polypeptide with the STF and the spleen cells of thymectomised mice in order to establish whether this polypeptide inhibits the effect of the thymic factor on these same cells.

The particularly interesting polypeptides which are antagonistic in vitro as regards STF are the polypeptides 42, 53, 59, 36, 79 and 66.

In addition, the polypeptides were subjected to the test No. 6, which consists in establishing homo-grafts, utilising mice of strain A as graft donor and mice of strain CBA as receiver.

The receiving mice were treated 8 days prior to grafting (3 injections per week) with 10 or 100 ng of STF bonded with carboxymethyl cellulose or a delay-action polypeptide not bonded with carboxymethyl cellulose. The control mice were treated only with carboxymethyl cellulose. The grafting was carried out on the eighth day of treatment, this being followed to the point of rejection. The STF and the delay-action polypeptides were found to be capable of very significantly retarding the rejection of the skin grafts.

The active polypeptides are capable of being used in place of the thymic hormone for therapeutic purposes, because of their better resistance to the degradation agents: These polypeptides consequently have the same therapeutic applications as the natural thymic hormone and are useful in the treatment of auto-immunisation diseases, such as the diseases of the Lupus type and specifically for the treatment of *Lupus erythematotus* which is found in human beings. These polypeptides are also useful for selectively stimulating the activity of the T cells during certain acute and chronic, bacterial and viral infections, and in connection with elderly people. These polypeptides could also find some purpose in the treatment of certain neoplastic states.

The inactive or very slightly active polypeptides generally show an inhibiting or antagonistic action as regards the thymic activity and act on the cells T by preventing them from serving their purpose of immunitary defence. These polypeptides can be used for reducing certain immunitary reactions, such as in the prevention of the rejection of grafts.

The novel polypeptides of the present invention may be administered intravenously or intramuscularly. Appropriate vehicles which can be employed in the composition comprise, for example, sterile liquids such as water or a physiological solution or substances which prolong the "life" of the peptides. As well as a vehicle, the present compositions may also comprise other ingredients, such as stabilisers, anti-oxidants, suspension agents or preservatives, such as phenol or chlorobutanol and the agents of like type. The final solution may be easily sterilised by the conventional filtration techniques.

The composition used in the present invention contains, in aqueous solution, a sufficient quantity of the therapeutic agent for being medically useful. The doses to be administered depend to a large degree on the condition of the subject who is being treated and the weight of the host. The parenteral route is preferred. In general, useful daily doses are between about 0.00001 mg and about 0.1 mg of active ingredient per kg of body weight of the subject and a single or several applications per day. Preferred daily doses are between about 0.0001 and about 0.001 of active ingredient per kg of body weight. An injectable dose which is of particular interest is a dose of 0.01 mg of active material administered every day. Using parenteral administration, the form of unit dosage is usually the pure compound in a sterile aqueous solution or in the form of a soluble powder provided for being dissolved.

The following examples describe a composition for parenteral administration, supplied in ampoules, in bottles and multiple dose bottles.

EXAMPLE 15

Parenteral Solution Containing 0.1 Mg of Polypeptide

Polypeptide: 0.1 mg
Sterile distilled water free pyrogens: 1.0 ml

Sterilised by filtration and made up in ampoules, bottles or multiple dose bottles.

EXAMPLE 16

Ampoules Containing 0.1 Mg of Lyophilised Polypeptide

Ampoule: Polypeptide: 0.1 mg
Ampoule: Diluent: sterile water for injection: 1 ml Appropriate multiples of the above quantities are used, depending on requirements.

What is claimed is:

1. A polypeptide having thymic activity selected from the group consisting of:

Ala-Lys-Ser-Gln-Gly-Gly-Ser-Asn,

Gln-Ala-Lys-Ser-Gln-Gly-Gly-Ser-Asn,

Z-Gln-Ala-Lys-Ser-Gln-Gly-Gly-Ser-Asn,

Lys-Ser-Gln-Gly-Gly-Ser-Asn,

PyroGlu-Ala-Lys-(Ac)-Ser-Gln-Gly-Gly-Ser-Asn,

PyroGlu-Ala-D-Lys-Ser-Gln-Gly-Gly-Ser-Asn,

PyroGlu-Ala-Lys-Ser-Gln-Gly-Gly-Ser-Ala-$NH_2$,

PyroGlu-Ala-Lys-Ser-Gln-D-Ala-Gly-Ser-Asn, or

PyroGlu-Ala-Lys-Ser-Gln-Gly-Gly-Ser-D-Asn.

2. A polypeptide having thymic inhibiting or antagonistic activity selected from the group consisting of:

PyroGlu-Ala-Lys-Ser-Gln-Gly-Gly-Ser,

PyroGlu-Ala-Lys-Ser-Gln-Gly-Gly-Ser-Asp,

PyroGlu-Ala-Lys-Ser-Gln-Gly-Gly-Ala-Asn, or

PyroGlu-Ala-Lys-Ser-Gln-Gly-Gly-Ser-Gln.

3. A biological composition having thymic activity which comprises a biologically acceptable carrier and an amount of a polypeptide of claim 1 effective to produce thymic activity.

4. The composition of claim 3 having thymic inhibiting or antagonistic activity wherein the polypeptide is selected from the group consisting of:

PyroGlu-Ala-Lys-Ser-Gln-Gly-Gly-Ser,

PyroGlu-Ala-Lys-Ser-Gln-Gly-Gly-Ser-Asp,

PyroGlu-Ala-Lys-Ser-Gln-Gly-Gly-Ala-Asn, or

PyroGlu-Ala-Lys-Ser-Gln-Gly-Gly-Ser-Gln.

* * * * *